(12) United States Patent
Gonzalez

(10) Patent No.: US 8,715,685 B2
(45) Date of Patent: May 6, 2014

(54) STEREOISOMER PEPTIDES AND THEIR POLYMER CONJUGATES FOR HIV DISEASE

(76) Inventor: Lucia Irene Gonzalez, Baltimore, MD (US)

(*) Notice: Subject to any disclaimer, the term of this patent is extended or adjusted under 35 U.S.C. 154(b) by 787 days.

(21) Appl. No.: 12/836,187

(22) Filed: Jul. 14, 2010

(65) Prior Publication Data

US 2011/0014222 A1  Jan. 20, 2011

Related U.S. Application Data

(60) Provisional application No. 61/213,345, filed on Jul. 14, 2009, provisional application No. 61/213,548, filed on Jul. 18, 2009.

(51) Int. Cl.
*C07K 4/02* (2006.01)
*C07K 7/00* (2006.01)
*C07K 7/02* (2006.01)
*C07K 7/50* (2006.01)
*C07K 11/02* (2006.01)
*C07K 14/16* (2006.01)
*C07K 17/08* (2006.01)

(52) U.S. Cl.
USPC ... 424/188.1; 530/345; 530/402; 424/196.11; 514/3.8; 514/772.3

(58) Field of Classification Search
None
See application file for complete search history.

(56) References Cited

U.S. PATENT DOCUMENTS

| | | |
|---|---|---|
| 6,440,461 B1 | 8/2002 | Bru-Magniez et al. |
| 7,141,540 B2 | 11/2006 | Wang et al. |
| 7,332,523 B2 | 2/2008 | Satchi-Fainaro et al. |
| 7,569,222 B2 | 8/2009 | Woerly |
| 7,662,360 B2 | 2/2010 | Patel |
| 2003/0032594 A1* | 2/2003 | Bonny .......................... 514/12 |
| 2003/0228634 A1* | 12/2003 | Simard et al. .................. 435/7.2 |
| 2006/0188469 A1* | 8/2006 | Turnell et al. .............. 424/78.27 |

FOREIGN PATENT DOCUMENTS

| | | | | |
|---|---|---|---|---|
| WO | WO 8901492 A1 * | 2/1989 | ............... | C07K 7/08 |
| WO | WO 9604373 A2 * | 2/1996 | ............. | C12N 15/10 |
| WO | WO 97/33618 | 9/1997 | | |
| WO | WO03066068 | 8/2003 | | |

OTHER PUBLICATIONS

Malugin et al. Liberation of Doxorubicin from HPMA Copolymer Conjugate is Essential for the Induction of Cell Cycle Arrest and Nuclear Fragmentation in Ovarian Carcinoma Cells. Journal of Controlled Release Dec. 4, 2007, vol. 124, No. 1-2, pp. 6-10.*

Maeda et al. "Conjugates of Anticancer Agents and Polymers: Advantages of Macromolecular Therapeutics in Vivo", 1992, 3(5):351-362.

Greco et al. "Polymer-drug Conjugates: Current Status and Future Trends", 2008, Front. Biosci. 13, 2744-2756.

\* cited by examiner

*Primary Examiner* — Louise Humphrey

(57) ABSTRACT

This invention discloses a group of 298 peptides from which several peptides are independently selected and synthesized in their stereoisomer and chemically modified forms, and conjugated to a polymer via linkers creating novel anti-HIV-1 multi-peptide-polymer conjugate compounds for the treatment and prevention of HIV-1 infection. The peptides mimic the domains of major HIV-1 proteins, and therefore, they function as inhibitors of the targeted HIV-1 proteins. The polymer is a useful delivery system for the stereoisomer peptides, and certain peptides are peptide-ligands for targeted delivery into the HIV infected cells.

14 Claims, 4 Drawing Sheets

SEQUENCE LISTING

<160> NUMBER OF SEQ ID NOS: 298

<210> SEQ ID NO 1
<211> LENGTH: 11
<212> TYPE: PRT
<213> ORGANISM: Human immunodeficiency virus type 1

```
<400> SEQUENCE: 1

Pro Ile Val Gln Asn Ile Gln Gly Glu Met Val
1               5                   10

<210> SEQ ID NO 2
<211> LENGTH: 11
<212> TYPE: PRT
<213> ORGANISM: Human immunodeficiency virus type 1

<400> SEQUENCE: 2

Tyr Pro Ile Val Gln Asn Ile Gln Gly Gln Met
1               5                   10

<210> SEQ ID NO 3
<211> LENGTH: 10
<212> TYPE: PRT
<213> ORGANISM: Human immunodeficiency virus type 1

<400> SEQUENCE: 3

Pro Ile Val Gln Asn Ile Gln Gly Gln Met
1               5                   10

<210> SEQ ID NO 4
<211> LENGTH: 9
<212> TYPE: PRT
<213> ORGANISM: Human immunodeficiency virus type 1

<400> SEQUENCE: 4

Gln Asn Ile Gln Gly Gln Met Val His
1               5

<210> SEQ ID NO 5
<211> LENGTH: 8
<212> TYPE: PRT
<213> ORGANISM: Human immunodeficiency virus type 1

<400> SEQUENCE: 5

Ile Leu Gly Leu Asn Lys Ile Val
1               5

<210> SEQ ID NO 6

<400> SEQUENCE: 6

000

<210> SEQ ID NO 7
<211> LENGTH: 9
<212> TYPE: PRT
<213> ORGANISM: Human immunodeficiency virus type 1

<400> SEQUENCE: 7

Ile Ile Leu Gly Leu Asx Lys Ile Val
1               5

<210> SEQ ID NO 8
<211> LENGTH: 9
<212> TYPE: PRT
<213> ORGANISM: Human immunodeficiency virus type 1

<400> SEQUENCE: 8

Tyr Lys Arg Trp Ile Ile Leu Gly Leu
1               5
```

```
<210> SEQ ID NO 9
<211> LENGTH: 10
<212> TYPE: PRT
<213> ORGANISM: Human immunodeficiency virus type 1

<400> SEQUENCE: 9

Trp Ile Ile Leu Gly Leu Asn Lys Ile Val
1               5                   10

<210> SEQ ID NO 10
<211> LENGTH: 11
<212> TYPE: PRT
<213> ORGANISM: Human immunodeficiency virus type 1

<400> SEQUENCE: 10

Lys Arg Trp Ile Ile Leu Gly Leu Asn Lys Ile
1               5                   10

<210> SEQ ID NO 11
<211> LENGTH: 15
<212> TYPE: PRT
<213> ORGANISM: Human immunodeficiency virus type 1

<400> SEQUENCE: 11

Tyr Lys Arg Trp Ile Ile Leu Gly Leu Asn Lys Ile Val Arg Met
1               5                   10                  15

<210> SEQ ID NO 12
<211> LENGTH: 9
<212> TYPE: PRT
<213> ORGANISM: Human immunodeficiency virus type 1

<400> SEQUENCE: 12

Trp Ile Ile Leu Gly Leu Asn Lys Ile
1               5

<210> SEQ ID NO 13
<211> LENGTH: 8
<212> TYPE: PRT
<213> ORGANISM: Human immunodeficiency virus type 1

<400> SEQUENCE: 13

Ser Gln Glu Val Lys Asn Trp Met
1               5

<210> SEQ ID NO 14
<211> LENGTH: 10
<212> TYPE: PRT
<213> ORGANISM: Human immunodeficiency virus type 1

<400> SEQUENCE: 14

Leu Gly Lys Ile Trp Pro Ser Tyr Lys Gly
1               5                   10

<210> SEQ ID NO 15
<211> LENGTH: 8
<212> TYPE: PRT
<213> ORGANISM: Human immunodeficiency virus type 1

<400> SEQUENCE: 15

Arg Ala Asn Ser Pro Thr Arg Arg
1               5

<210> SEQ ID NO 16
<211> LENGTH: 8
<212> TYPE: PRT
```

```
<213> ORGANISM: Human immunodeficiency virus type 1

<400> SEQUENCE: 16

Thr Arg Arg Glu Leu Gln Val Trp
1               5

<210> SEQ ID NO 17
<211> LENGTH: 8
<212> TYPE: PRT
<213> ORGANISM: Human immunodeficiency virus type 1

<400> SEQUENCE: 17

Asn Ser Pro Thr Arg Arg Glu Leu
1               5

<210> SEQ ID NO 18
<211> LENGTH: 9
<212> TYPE: PRT
<213> ORGANISM: Human immunodeficiency virus type 1

<400> SEQUENCE: 18

Gln Thr Arg Ala Asn Ser Pro Thr Arg
1               5

<210> SEQ ID NO 19
<211> LENGTH: 9
<212> TYPE: PRT
<213> ORGANISM: Human immunodeficiency virus type 1

<400> SEQUENCE: 19

Pro Thr Arg Arg Glu Leu Gln Val Trp
1               5

<210> SEQ ID NO 20
<211> LENGTH: 10
<212> TYPE: PRT
<213> ORGANISM: Human immunodeficiency virus type 1

<400> SEQUENCE: 20

Gln Thr Arg Ala Asn Ser Pro Thr Arg Arg
1               5                   10

<210> SEQ ID NO 21
<211> LENGTH: 10
<212> TYPE: PRT
<213> ORGANISM: Human immunodeficiency virus type 1

<400> SEQUENCE: 21

Ser Pro Thr Arg Arg Glu Leu Gln Val Trp
1               5                   10

<210> SEQ ID NO 22
<211> LENGTH: 15
<212> TYPE: PRT
<213> ORGANISM: Human immunodeficiency virus type 1

<400> SEQUENCE: 22

Leu Gln Val Trp Gly Arg Asp Asn Asn Ser Pro Ser Glu Ala Gly
1               5                   10                  15

<210> SEQ ID NO 23
<211> LENGTH: 9
<212> TYPE: PRT
<213> ORGANISM: Human immunodeficiency virus type 1

<400> SEQUENCE: 23
```

```
Thr Arg Ala Asn Ser Pro Thr Arg Arg
1               5

<210> SEQ ID NO 24
<211> LENGTH: 9
<212> TYPE: PRT
<213> ORGANISM: Human immunodeficiency virus type 1

<400> SEQUENCE: 24

Arg Arg Glu Leu Gln Val Trp Gly Arg
1               5

<210> SEQ ID NO 25
<211> LENGTH: 8
<212> TYPE: PRT
<213> ORGANISM: Human immunodeficiency virus type 1

<400> SEQUENCE: 25

Thr Leu Trp Gln Arg Pro Leu Val
1               5

<210> SEQ ID NO 26
<211> LENGTH: 8
<212> TYPE: PRT
<213> ORGANISM: Human immunodeficiency virus type 1

<400> SEQUENCE: 26

Trp Gln Arg Pro Leu Val Thr Ile
1               5

<210> SEQ ID NO 27
<211> LENGTH: 8
<212> TYPE: PRT
<213> ORGANISM: Human immunodeficiency virus type 1

<400> SEQUENCE: 27

Thr Leu Trp Gln Arg Pro Leu Val
1               5

<210> SEQ ID NO 28
<211> LENGTH: 8
<212> TYPE: PRT
<213> ORGANISM: Human immunodeficiency virus type 1

<400> SEQUENCE: 28

Thr Val Leu Glu Glu Met Ser Leu
1               5

<210> SEQ ID NO 29
<211> LENGTH: 9
<212> TYPE: PRT
<213> ORGANISM: Human immunodeficiency virus type 1

<400> SEQUENCE: 29

Val Thr Leu Trp Gln Arg Pro Leu Val
1               5

<210> SEQ ID NO 30
<211> LENGTH: 9
<212> TYPE: PRT
<213> ORGANISM: Human immunodeficiency virus type 1

<400> SEQUENCE: 30

Ser Leu Pro Gly Arg Trp Lys Pro Lys
1               5
```

<210> SEQ ID NO 31
<211> LENGTH: 10
<212> TYPE: PRT
<213> ORGANISM: Human immunodeficiency virus type 1

<400> SEQUENCE: 31

Leu Leu Asp Thr Gly Ala Asp Asp Thr Val
1               5                   10

<210> SEQ ID NO 32
<211> LENGTH: 10
<212> TYPE: PRT
<213> ORGANISM: Human immunodeficiency virus type 1

<400> SEQUENCE: 32

Thr Leu Trp Gln Arg Pro Leu Val Thr Ile
1               5                   10

<210> SEQ ID NO 33
<211> LENGTH: 10
<212> TYPE: PRT
<213> ORGANISM: Human immunodeficiency virus type 1

<400> SEQUENCE: 33

Ser Leu Pro Gly Arg Trp Lys Pro Lys Met
1               5                   10

<210> SEQ ID NO 34
<211> LENGTH: 10
<212> TYPE: PRT
<213> ORGANISM: Human immunodeficiency virus type 1

<400> SEQUENCE: 34

Val Thr Ile Lys Ile Gly Gly Gln Leu Lys
1               5                   10

<210> SEQ ID NO 35
<211> LENGTH: 10
<212> TYPE: PRT
<213> ORGANISM: Human immunodeficiency virus type 1

<400> SEQUENCE: 35

Met Ser Leu Pro Gly Arg Trp Lys Pro Lys
1               5                   10

<210> SEQ ID NO 36
<211> LENGTH: 10
<212> TYPE: PRT
<213> ORGANISM: Human immunodeficiency virus type 1

<400> SEQUENCE: 36

Leu Pro Gly Arg Trp Lys Pro Lys Met Ile
1               5                   10

<210> SEQ ID NO 37
<211> LENGTH: 10
<212> TYPE: PRT
<213> ORGANISM: Human immunodeficiency virus type 1

<400> SEQUENCE: 37

Trp Gln Arg Pro Leu Val Thr Ile Lys Ile
1               5                   10

<210> SEQ ID NO 38

```
<211> LENGTH: 11
<212> TYPE: PRT
<213> ORGANISM: Human immunodeficiency virus type 1

<400> SEQUENCE: 38

Ala Leu Leu Asp Thr Gly Ala Asp Asp Thr Val
1               5                   10

<210> SEQ ID NO 39
<211> LENGTH: 11
<212> TYPE: PRT
<213> ORGANISM: Human immunodeficiency virus type 1

<400> SEQUENCE: 39

Gln Leu Lys Glu Ala Leu Leu Asp Thr Gly Ala
1               5                   10

<210> SEQ ID NO 40
<211> LENGTH: 10
<212> TYPE: PRT
<213> ORGANISM: Human immunodeficiency virus type 1

<400> SEQUENCE: 40

Leu Leu Asp Thr Gly Ala Asp Asp Thr Val
1               5                   10

<210> SEQ ID NO 41
<211> LENGTH: 11
<212> TYPE: PRT
<213> ORGANISM: Human immunodeficiency virus type 1

<400> SEQUENCE: 41

Ser Leu Pro Gly Arg Trp Lys Pro Lys Met Ile
1               5                   10

<210> SEQ ID NO 42
<211> LENGTH: 11
<212> TYPE: PRT
<213> ORGANISM: Human immunodeficiency virus type 1

<400> SEQUENCE: 42

Thr Leu Trp Gln Arg Pro Leu Val Thr Ile Lys
1               5                   10

<210> SEQ ID NO 43
<211> LENGTH: 11
<212> TYPE: PRT
<213> ORGANISM: Human immunodeficiency virus type 1

<400> SEQUENCE: 43

Thr Val Leu Glu Glu Met Ser Leu Pro Gly Arg
1               5                   10

<210> SEQ ID NO 44
<211> LENGTH: 11
<212> TYPE: PRT
<213> ORGANISM: Human immunodeficiency virus type 1

<400> SEQUENCE: 44

Met Ser Leu Pro Gly Arg Trp Lys Pro Lys Met
1               5                   10

<210> SEQ ID NO 45
<211> LENGTH: 11
<212> TYPE: PRT
<213> ORGANISM: Human immunodeficiency virus type 1
```

<400> SEQUENCE: 45

Gly Arg Trp Lys Pro Lys Met Ile Gly Gly Ile
1               5                   10

<210> SEQ ID NO 46
<211> LENGTH: 15
<212> TYPE: PRT
<213> ORGANISM: Human immunodeficiency virus type 1

<400> SEQUENCE: 46

Thr Gly Ala Asp Asp Thr Val Leu Glu Glu Met Ser Leu Pro Gly
1               5                   10                  15

<210> SEQ ID NO 47
<211> LENGTH: 16
<212> TYPE: PRT
<213> ORGANISM: Human immunodeficiency virus type 1

<400> SEQUENCE: 47

Arg Pro Leu Val Thr Ile Lys Ile Gly Gly Gln Leu Lys Glu Ala Ser
1               5                   10                  15

<210> SEQ ID NO 48
<211> LENGTH: 9
<212> TYPE: PRT
<213> ORGANISM: Human immunodeficiency virus type 1

<400> SEQUENCE: 48

Asp Thr Val Leu Glu Glu Met Ser Leu
1               5

<210> SEQ ID NO 49
<211> LENGTH: 8
<212> TYPE: PRT
<213> ORGANISM: Human immunodeficiency virus type 1

<400> SEQUENCE: 49

Glu Arg Ala Glu Asp Ser Gly Asn
1               5

<210> SEQ ID NO 50
<211> LENGTH: 8
<212> TYPE: PRT
<213> ORGANISM: Human immunodeficiency virus type 1

<400> SEQUENCE: 50

Tyr Gln Leu Glu Lys Glu Pro Ile
1               5

<210> SEQ ID NO 51
<211> LENGTH: 8
<212> TYPE: PRT
<213> ORGANISM: Human immunodeficiency virus type 1

<400> SEQUENCE: 51

Gln Leu Glu Lys Glu Pro Ile Val
1               5

<210> SEQ ID NO 52
<211> LENGTH: 8
<212> TYPE: PRT
<213> ORGANISM: Human immunodeficiency virus type 1

<400> SEQUENCE: 52

```
Lys Leu Trp Tyr Gln Leu Glu Lys
1               5

<210> SEQ ID NO 53
<211> LENGTH: 8
<212> TYPE: PRT
<213> ORGANISM: Human immunodeficiency virus type 1

<400> SEQUENCE: 53

Tyr Val Asp Gly Ala Ala Asn Arg
1               5

<210> SEQ ID NO 54
<211> LENGTH: 8
<212> TYPE: PRT
<213> ORGANISM: Human immunodeficiency virus type 1

<400> SEQUENCE: 54

Glu Thr Phe Tyr Val Asp Gly Ala
1               5

<210> SEQ ID NO 55
<211> LENGTH: 9
<212> TYPE: PRT
<213> ORGANISM: Human immunodeficiency virus type 1

<400> SEQUENCE: 55

Ile Val Gly Ala Glu Thr Phe Tyr Val
1               5

<210> SEQ ID NO 56
<211> LENGTH: 9
<212> TYPE: PRT
<213> ORGANISM: Human immunodeficiency virus type 1

<400> SEQUENCE: 56

Tyr Gln Leu Glu Lys Glu Pro Ile Val
1               5

<210> SEQ ID NO 57
<211> LENGTH: 9
<212> TYPE: PRT
<213> ORGANISM: Human immunodeficiency virus type 1

<400> SEQUENCE: 57

Pro Ile Val Gly Ala Glu Thr Phe Tyr
1               5

<210> SEQ ID NO 58
<211> LENGTH: 9
<212> TYPE: PRT
<213> ORGANISM: Human immunodeficiency virus type 1

<400> SEQUENCE: 58

Phe Tyr Val Asp Gly Ala Ala Asn Arg
1               5

<210> SEQ ID NO 59
<211> LENGTH: 9
<212> TYPE: PRT
<213> ORGANISM: Human immunodeficiency virus type 1

<400> SEQUENCE: 59

Glu Thr Phe Tyr Val Asp Gly Ala Ala
1               5
```

```
<210> SEQ ID NO 60
<211> LENGTH: 9
<212> TYPE: PRT
<213> ORGANISM: Human immunodeficiency virus type 1

<400> SEQUENCE: 60

Ile Val Gly Ala Glu Thr Phe Tyr Val
1               5

<210> SEQ ID NO 61
<211> LENGTH: 9
<212> TYPE: PRT
<213> ORGANISM: Human immunodeficiency virus type 1

<400> SEQUENCE: 61

Glu Pro Ile Val Gly Ala Glu Thr Phe
1               5

<210> SEQ ID NO 62
<211> LENGTH: 9
<212> TYPE: PRT
<213> ORGANISM: Human immunodeficiency virus type 1

<400> SEQUENCE: 62

Tyr Val Asp Gly Ala Ala Asn Arg Glu
1               5

<210> SEQ ID NO 63
<211> LENGTH: 10
<212> TYPE: PRT
<213> ORGANISM: Human immunodeficiency virus type 1

<400> SEQUENCE: 63

Pro Ile Val Gly Ala Glu Thr Phe Tyr Val
1               5                   10

<210> SEQ ID NO 64
<211> LENGTH: 10
<212> TYPE: PRT
<213> ORGANISM: Human immunodeficiency virus type 1

<400> SEQUENCE: 64

Glu Pro Ile Val Gly Ala Glu Thr Phe Tyr
1               5                   10

<210> SEQ ID NO 65
<211> LENGTH: 10
<212> TYPE: PRT
<213> ORGANISM: Human immunodeficiency virus type 1

<400> SEQUENCE: 65

Thr Phe Tyr Val Asp Gly Ala Ala Asn Arg
1               5                   10

<210> SEQ ID NO 66
<211> LENGTH: 10
<212> TYPE: PRT
<213> ORGANISM: Human immunodeficiency virus type 1

<400> SEQUENCE: 66

Tyr Val Asp Gly Ala Ala Asn Arg Glu Thr
1               5                   10

<210> SEQ ID NO 67
<211> LENGTH: 11
```

```
<212> TYPE: PRT
<213> ORGANISM: Human immunodeficiency virus type 1

<400> SEQUENCE: 67

Tyr Gln Leu Glu Lys Glu Pro Ile Val Gly Ala
1               5                   10

<210> SEQ ID NO 68
<211> LENGTH: 11
<212> TYPE: PRT
<213> ORGANISM: Human immunodeficiency virus type 1

<400> SEQUENCE: 68

Tyr Gln Leu Glu Lys Glu Pro Ile Val Gly Ala
1               5                   10

<210> SEQ ID NO 69
<211> LENGTH: 11
<212> TYPE: PRT
<213> ORGANISM: Human immunodeficiency virus type 1

<400> SEQUENCE: 69

Glu Thr Phe Tyr Val Asp Gly Ala Ala Asn Arg
1               5                   10

<210> SEQ ID NO 70
<211> LENGTH: 11
<212> TYPE: PRT
<213> ORGANISM: Human immunodeficiency virus type 1

<400> SEQUENCE: 70

Glu Pro Ile Val Gly Ala Glu Thr Phe Tyr Val
1               5                   10

<210> SEQ ID NO 71
<211> LENGTH: 15
<212> TYPE: PRT
<213> ORGANISM: Human immunodeficiency virus type 1

<400> SEQUENCE: 71

Lys Glu Pro Ile Val Gly Ala Glu Thr Phe Tyr Val Asp Gly Ala
1               5                   10                  15

<210> SEQ ID NO 72
<211> LENGTH: 15
<212> TYPE: PRT
<213> ORGANISM: Human immunodeficiency virus type 1

<400> SEQUENCE: 72

Val Lys Leu Trp Tyr Gln Leu Glu Lys Glu Pro Ile Val Gly Ala
1               5                   10                  15

<210> SEQ ID NO 73
<211> LENGTH: 8
<212> TYPE: PRT
<213> ORGANISM: Human immunodeficiency virus type 1

<400> SEQUENCE: 73

His Pro Arg Ile Ser Ser Glu Val
1               5

<210> SEQ ID NO 74
<211> LENGTH: 9
<212> TYPE: PRT
<213> ORGANISM: Human immunodeficiency virus type 1
```

<400> SEQUENCE: 74

Ile Ser Ser Glu Val His Ile Pro Leu
1               5

<210> SEQ ID NO 75
<211> LENGTH: 10
<212> TYPE: PRT
<213> ORGANISM: Human immunodeficiency virus type 1

<400> SEQUENCE: 75

Arg Ile Ser Ser Glu Val His Ile Pro Leu
1               5                   10

<210> SEQ ID NO 76
<211> LENGTH: 10
<212> TYPE: PRT
<213> ORGANISM: Human immunodeficiency virus type 1

<400> SEQUENCE: 76

His Pro Arg Ile Ser Ser Glu Val His Ile
1               5                   10

<210> SEQ ID NO 77
<211> LENGTH: 9
<212> TYPE: PRT
<213> ORGANISM: Human immunodeficiency virus type 1

<400> SEQUENCE: 77

Pro Arg Ile Ser Ser Glu Val His Ile
1               5

<210> SEQ ID NO 78
<211> LENGTH: 8
<212> TYPE: PRT
<213> ORGANISM: Human immunodeficiency virus type 1

<400> SEQUENCE: 78

Gly Val Ser Ile Glu Trp Arg Lys
1               5

<210> SEQ ID NO 79
<211> LENGTH: 9
<212> TYPE: PRT
<213> ORGANISM: Human immunodeficiency virus type 1

<400> SEQUENCE: 79

Ser Ile Glu Trp Arg Lys Lys Arg Tyr
1               5

<210> SEQ ID NO 80
<211> LENGTH: 9
<212> TYPE: PRT
<213> ORGANISM: Human immunodeficiency virus type 1

<400> SEQUENCE: 80

Gly Val Ser Ile Glu Trp Arg Lys Lys
1               5

<210> SEQ ID NO 81
<211> LENGTH: 10
<212> TYPE: PRT
<213> ORGANISM: Human immunodeficiency virus type 1

<400> SEQUENCE: 81

Val Ser Ile Glu Trp Arg Lys Lys Arg Tyr

```
1               5                   10
```

<210> SEQ ID NO 82
<211> LENGTH: 8
<212> TYPE: PRT
<213> ORGANISM: Human immunodeficiency virus type 1

<400> SEQUENCE: 82

Ile Glu Trp Arg Lys Lys Arg Tyr
1               5

<210> SEQ ID NO 83
<211> LENGTH: 8
<212> TYPE: PRT
<213> ORGANISM: Human immunodeficiency virus type 1

<400> SEQUENCE: 83

Met Glu Gln Ala Pro Glu Asp Gln
1               5

<210> SEQ ID NO 84
<211> LENGTH: 8
<212> TYPE: PRT
<213> ORGANISM: Human immunodeficiency virus type 1

<400> SEQUENCE: 84

Arg Ile Gly Cys Arg His Ser Arg
1               5

<210> SEQ ID NO 85
<211> LENGTH: 8
<212> TYPE: PRT
<213> ORGANISM: Human immunodeficiency virus type 1

<400> SEQUENCE: 85

Arg Ala Arg Asn Gly Ala Ser Arg
1               5

<210> SEQ ID NO 86
<211> LENGTH: 8
<212> TYPE: PRT
<213> ORGANISM: Human immunodeficiency virus type 1

<400> SEQUENCE: 86

Val Thr Arg Gln Arg Arg Ala Arg
1               5

<210> SEQ ID NO 87
<211> LENGTH: 8
<212> TYPE: PRT
<213> ORGANISM: Human immunodeficiency virus type 1

<400> SEQUENCE: 87

His Ser Arg Ile Gly Val Thr Arg
1               5

<210> SEQ ID NO 88
<211> LENGTH: 8
<212> TYPE: PRT
<213> ORGANISM: Human immunodeficiency virus type 1

<400> SEQUENCE: 88

Arg Ile Gly Val Thr Arg Gln Arg
1               5

-continued

```
<210> SEQ ID NO 89
<211> LENGTH: 9
<212> TYPE: PRT
<213> ORGANISM: Human immunodeficiency virus type 1

<400> SEQUENCE: 89

Arg Ile Gly Val Thr Arg Gln Arg Arg
1               5

<210> SEQ ID NO 90
<211> LENGTH: 9
<212> TYPE: PRT
<213> ORGANISM: Human immunodeficiency virus type 1

<400> SEQUENCE: 90

Gly Val Thr Arg Gln Arg Arg Ala Arg
1               5

<210> SEQ ID NO 91
<211> LENGTH: 10
<212> TYPE: PRT
<213> ORGANISM: Human immunodeficiency virus type 1

<400> SEQUENCE: 91

His Phe Arg Ile Gly Cys Arg His Ser Arg
1               5                   10

<210> SEQ ID NO 92
<211> LENGTH: 11
<212> TYPE: PRT
<213> ORGANISM: Human immunodeficiency virus type 1

<400> SEQUENCE: 92

Arg Ile Gly Cys Arg His Ser Arg Ile Gly Val
1               5                   10

<210> SEQ ID NO 93
<211> LENGTH: 11
<212> TYPE: PRT
<213> ORGANISM: Human immunodeficiency virus type 1

<400> SEQUENCE: 93

Arg Gln Arg Arg Ala Arg Asn Gly Ala Ser Arg
1               5                   10

<210> SEQ ID NO 94
<211> LENGTH: 11
<212> TYPE: PRT
<213> ORGANISM: Human immunodeficiency virus type 1

<400> SEQUENCE: 94

His Ser Arg Ile Gly Val Thr Arg Gln Arg Arg
1               5                   10

<210> SEQ ID NO 95
<211> LENGTH: 11
<212> TYPE: PRT
<213> ORGANISM: Human immunodeficiency virus type 1

<400> SEQUENCE: 95

Arg Ile Gly Val Thr Arg Gln Arg Arg Ala Arg
1               5                   10

<210> SEQ ID NO 96
<211> LENGTH: 9
<212> TYPE: PRT
```

<213> ORGANISM: Human immunodeficiency virus type 1

<400> SEQUENCE: 96

Arg Arg Ala Arg Asn Gly Ala Ser Arg
1               5

<210> SEQ ID NO 97
<211> LENGTH: 9
<212> TYPE: PRT
<213> ORGANISM: Human immunodeficiency virus type 1

<400> SEQUENCE: 97

Phe Arg Ile Gly Cys Arg His Ser Arg
1               5

<210> SEQ ID NO 98
<211> LENGTH: 9
<212> TYPE: PRT
<213> ORGANISM: Human immunodeficiency virus type 1

<400> SEQUENCE: 98

Arg His Ser Arg Ile Gly Val Thr Arg
1               5

<210> SEQ ID NO 99
<211> LENGTH: 9
<212> TYPE: PRT
<213> ORGANISM: Human immunodeficiency virus type 1

<400> SEQUENCE: 99

Ser Arg Ile Gly Val Thr Arg Gln Arg
1               5

<210> SEQ ID NO 100
<211> LENGTH: 8
<212> TYPE: PRT
<213> ORGANISM: Human immunodeficiency virus type 1

<400> SEQUENCE: 100

Phe Ile Thr Lys Ala Leu Gly Ile
1               5

<210> SEQ ID NO 101
<211> LENGTH: 9
<212> TYPE: PRT
<213> ORGANISM: Human immunodeficiency virus type 1

<400> SEQUENCE: 101

Lys Ala Leu Gly Ile Ser Tyr Gly Arg
1               5

<210> SEQ ID NO 102
<211> LENGTH: 9
<212> TYPE: PRT
<213> ORGANISM: Human immunodeficiency virus type 1

<400> SEQUENCE: 102

Ile Thr Lys Ala Leu Gly Ile Ser Tyr
1               5

<210> SEQ ID NO 103
<211> LENGTH: 10
<212> TYPE: PRT
<213> ORGANISM: Human immunodeficiency virus type 1

<400> SEQUENCE: 103

```
Phe Ile Thr Lys Ala Leu Gly Ile Ser Tyr
1               5                   10

<210> SEQ ID NO 104
<211> LENGTH: 11
<212> TYPE: PRT
<213> ORGANISM: Human immunodeficiency virus type 1

<400> SEQUENCE: 104

Ile Thr Lys Ala Leu Gly Ile Ser Tyr Gly Arg
1               5                   10

<210> SEQ ID NO 105
<211> LENGTH: 11
<212> TYPE: PRT
<213> ORGANISM: Human immunodeficiency virus type 1

<400> SEQUENCE: 105

Gln Arg Arg Gln Asp Ile Leu Asp Leu Trp Ile
1               5                   10

<210> SEQ ID NO 106
<211> LENGTH: 9
<212> TYPE: PRT
<213> ORGANISM: Human immunodeficiency virus type 1

<400> SEQUENCE: 106

Arg Arg Gln Asp Ile Leu Asp Leu Trp
1               5

<210> SEQ ID NO 107
<211> LENGTH: 9
<212> TYPE: PRT
<213> ORGANISM: Human immunodeficiency virus type 1

<400> SEQUENCE: 107

Arg Gln Asp Ile Leu Asp Leu Trp Ile
1               5

<210> SEQ ID NO 108
<211> LENGTH: 9
<212> TYPE: PRT
<213> ORGANISM: Human immunodeficiency virus type 1

<400> SEQUENCE: 108

Gln Arg Arg Gln Asp Ile Leu Asp Leu
1               5

<210> SEQ ID NO 109
<211> LENGTH: 10
<212> TYPE: PRT
<213> ORGANISM: Human immunodeficiency virus type 1

<400> SEQUENCE: 109

Gln Arg Arg Gln Asp Ile Leu Asp Leu Trp
1               5                   10

<210> SEQ ID NO 110
<211> LENGTH: 10
<212> TYPE: PRT
<213> ORGANISM: Human immunodeficiency virus type 1

<400> SEQUENCE: 110

Arg Arg Gln Asp Ile Leu Asp Leu Trp Ile
1               5                   10
```

<210> SEQ ID NO 111
<211> LENGTH: 8
<212> TYPE: PRT
<213> ORGANISM: Human immunodeficiency virus type 1

<400> SEQUENCE: 111

Arg Arg Gln Asp Ile Leu Asp Leu
1               5

<210> SEQ ID NO 112
<211> LENGTH: 10
<212> TYPE: PRT
<213> ORGANISM: Human immunodeficiency virus type 1

<400> SEQUENCE: 112

Glu His His Val Ala Arg Glu Leu His Pro
1               5                   10

<210> SEQ ID NO 113
<211> LENGTH: 9
<212> TYPE: PRT
<213> ORGANISM: Human immunodeficiency virus type 1

<400> SEQUENCE: 113

Leu Val Pro Val Glu Pro Asp Lys Ile
1               5

<210> SEQ ID NO 114
<211> LENGTH: 11
<212> TYPE: PRT
<213> ORGANISM: Human immunodeficiency virus type 1

<400> SEQUENCE: 114

Leu Leu Lys Leu Ala Gly Arg Trp Pro Val Lys
1               5                   10

<210> SEQ ID NO 115
<211> LENGTH: 11
<212> TYPE: PRT
<213> ORGANISM: Human immunodeficiency virus type 1

<400> SEQUENCE: 115

Thr Ala Tyr Phe Leu Leu Lys Leu Ala Gly Arg
1               5                   10

<210> SEQ ID NO 116
<211> LENGTH: 11
<212> TYPE: PRT
<213> ORGANISM: Human immunodeficiency virus type 1

<400> SEQUENCE: 116

Glu Thr Gly Gln Glu Thr Ala Tyr Phe Leu Leu
1               5                   10

<210> SEQ ID NO 117
<211> LENGTH: 11
<212> TYPE: PRT
<213> ORGANISM: Human immunodeficiency virus type 1

<400> SEQUENCE: 117

Ile Pro Ala Glu Thr Gly Gln Glu Thr Ala Tyr
1               5                   10

<210> SEQ ID NO 118

```
<211> LENGTH: 11
<212> TYPE: PRT
<213> ORGANISM: Human immunodeficiency virus type 1

<400> SEQUENCE: 118

Ala Glu Thr Gly Gln Glu Thr Ala Tyr Phe Leu
1               5                   10

<210> SEQ ID NO 119
<211> LENGTH: 15
<212> TYPE: PRT
<213> ORGANISM: Human immunodeficiency virus type 1

<400> SEQUENCE: 119

Ala Tyr Phe Leu Leu Lys Leu Ala Gly Arg Trp Pro Val Lys Thr
1               5                   10                  15

<210> SEQ ID NO 120
<211> LENGTH: 9
<212> TYPE: PRT
<213> ORGANISM: Human immunodeficiency virus type 1

<400> SEQUENCE: 120

Lys Leu Ala Gly Arg Trp Pro Val Lys
1               5

<210> SEQ ID NO 121
<211> LENGTH: 9
<212> TYPE: PRT
<213> ORGANISM: Human immunodeficiency virus type 1

<400> SEQUENCE: 121

Glu Thr Ala Tyr Phe Leu Leu Lys Leu
1               5

<210> SEQ ID NO 122
<211> LENGTH: 9
<212> TYPE: PRT
<213> ORGANISM: Human immunodeficiency virus type 1

<400> SEQUENCE: 122

Leu Glu Gly Lys Val Ile Leu Val Ala
1               5

<210> SEQ ID NO 123
<211> LENGTH: 9
<212> TYPE: PRT
<213> ORGANISM: Human immunodeficiency virus type 1

<400> SEQUENCE: 123

Tyr Asn Pro Gln Ser Gln Gly Val Val
1               5

<210> SEQ ID NO 124
<211> LENGTH: 15
<212> TYPE: PRT
<213> ORGANISM: Human immunodeficiency virus type 1

<400> SEQUENCE: 124

Phe Lys Arg Lys Gly Gly Ile Gly Gly Tyr Ser Ala Gly Glu Arg
1               5                   10                  15

<210> SEQ ID NO 125
<211> LENGTH: 9
<212> TYPE: PRT
<213> ORGANISM: Human immunodeficiency virus type 1
```

<400> SEQUENCE: 125

Lys Arg Lys Gly Gly Ile Gly Gly Tyr
1               5

<210> SEQ ID NO 126
<211> LENGTH: 10
<212> TYPE: PRT
<213> ORGANISM: Human immunodeficiency virus type 1

<400> SEQUENCE: 126

Phe Lys Arg Lys Gly Gly Ile Gly Gly Tyr
1               5                   10

<210> SEQ ID NO 127
<211> LENGTH: 8
<212> TYPE: PRT
<213> ORGANISM: Human immunodeficiency virus type 1

<400> SEQUENCE: 127

Gly Glu Gly Ala Val Val Ile Gln
1               5

<210> SEQ ID NO 128
<211> LENGTH: 8
<212> TYPE: PRT
<213> ORGANISM: Human immunodeficiency virus type 1

<400> SEQUENCE: 128

Lys Leu Ala Gly Arg Trp Pro Val
1               5

<210> SEQ ID NO 129
<211> LENGTH: 8
<212> TYPE: PRT
<213> ORGANISM: Human immunodeficiency virus type 1

<400> SEQUENCE: 129

Ile Leu Val Ala Val His Val Ala
1               5

<210> SEQ ID NO 130
<211> LENGTH: 8
<212> TYPE: PRT
<213> ORGANISM: Human immunodeficiency virus type 1

<400> SEQUENCE: 130

Val Ile Leu Val Ala Val His Val
1               5

<210> SEQ ID NO 131
<211> LENGTH: 8
<212> TYPE: PRT
<213> ORGANISM: Human immunodeficiency virus type 1

<400> SEQUENCE: 131

His Leu Glu Gly Lys Val Ile Leu
1               5

<210> SEQ ID NO 132
<211> LENGTH: 8
<212> TYPE: PRT
<213> ORGANISM: Human immunodeficiency virus type 1

<400> SEQUENCE: 132

```
Glu Thr Ala Tyr Phe Leu Leu Lys
1               5

<210> SEQ ID NO 133
<211> LENGTH: 8
<212> TYPE: PRT
<213> ORGANISM: Human immunodeficiency virus type 1

<400> SEQUENCE: 133

Glu Thr Gly Gln Glu Thr Ala Tyr
1               5

<210> SEQ ID NO 134
<211> LENGTH: 8
<212> TYPE: PRT
<213> ORGANISM: Human immunodeficiency virus type 1

<400> SEQUENCE: 134

Gln Glu Thr Ala Tyr Phe Leu Leu
1               5

<210> SEQ ID NO 135
<211> LENGTH: 8
<212> TYPE: PRT
<213> ORGANISM: Human immunodeficiency virus type 1

<400> SEQUENCE: 135

Gly Arg Trp Pro Val Lys Thr Ile
1               5

<210> SEQ ID NO 136
<211> LENGTH: 9
<212> TYPE: PRT
<213> ORGANISM: Human immunodeficiency virus type 1

<400> SEQUENCE: 136

Lys Val Ile Leu Val Ala Val His Val
1               5

<210> SEQ ID NO 137
<211> LENGTH: 9
<212> TYPE: PRT
<213> ORGANISM: Human immunodeficiency virus type 1

<400> SEQUENCE: 137

His Leu Glu Gly Lys Val Ile Leu Val
1               5

<210> SEQ ID NO 138
<211> LENGTH: 9
<212> TYPE: PRT
<213> ORGANISM: Human immunodeficiency virus type 1

<400> SEQUENCE: 138

Leu Lys Leu Ala Gly Arg Trp Pro Val
1               5

<210> SEQ ID NO 139
<211> LENGTH: 9
<212> TYPE: PRT
<213> ORGANISM: Human immunodeficiency virus type 1

<400> SEQUENCE: 139

Lys Leu Ala Gly Arg Trp Pro Val Lys
1               5
```

<210> SEQ ID NO 140
<211> LENGTH: 9
<212> TYPE: PRT
<213> ORGANISM: Human immunodeficiency virus type 1

<400> SEQUENCE: 140

Glu Thr Gly Gln Glu Thr Ala Tyr Phe
1               5

<210> SEQ ID NO 141
<211> LENGTH: 9
<212> TYPE: PRT
<213> ORGANISM: Human immunodeficiency virus type 1

<400> SEQUENCE: 141

Glu Thr Ala Tyr Phe Leu Leu Lys Leu
1               5

<210> SEQ ID NO 142
<211> LENGTH: 9
<212> TYPE: PRT
<213> ORGANISM: Human immunodeficiency virus type 1

<400> SEQUENCE: 142

Tyr Phe Leu Leu Lys Leu Ala Gly Arg
1               5

<210> SEQ ID NO 143
<211> LENGTH: 9
<212> TYPE: PRT
<213> ORGANISM: Human immunodeficiency virus type 1

<400> SEQUENCE: 143

His Val Ala Ser Gly Tyr Ile Glu Ala
1               5

<210> SEQ ID NO 144
<211> LENGTH: 10
<212> TYPE: PRT
<213> ORGANISM: Human immunodeficiency virus type 1

<400> SEQUENCE: 144

Leu Leu Lys Leu Ala Gly Arg Trp Pro Val
1               5                   10

<210> SEQ ID NO 145
<211> LENGTH: 10
<212> TYPE: PRT
<213> ORGANISM: Human immunodeficiency virus type 1

<400> SEQUENCE: 145

Val Ala Ser Gly Tyr Ile Glu Ala Glu Val
1               5                   10

<210> SEQ ID NO 146
<211> LENGTH: 10
<212> TYPE: PRT
<213> ORGANISM: Human immunodeficiency virus type 1

<400> SEQUENCE: 146

His Leu Glu Gly Lys Val Ile Leu Val Ala
1               5                   10

<210> SEQ ID NO 147
<211> LENGTH: 10

-continued

```
<212> TYPE: PRT
<213> ORGANISM: Human immunodeficiency virus type 1

<400> SEQUENCE: 147

Gly Gln Glu Thr Ala Tyr Phe Leu Leu Lys
1               5                   10

<210> SEQ ID NO 148
<211> LENGTH: 10
<212> TYPE: PRT
<213> ORGANISM: Human immunodeficiency virus type 1

<400> SEQUENCE: 148

Tyr Phe Leu Leu Lys Leu Ala Gly Arg Trp
1               5                   10

<210> SEQ ID NO 149
<211> LENGTH: 10
<212> TYPE: PRT
<213> ORGANISM: Human immunodeficiency virus type 1

<400> SEQUENCE: 149

Leu Val Ala Val His Val Ala Ser Gly Tyr
1               5                   10

<210> SEQ ID NO 150
<211> LENGTH: 10
<212> TYPE: PRT
<213> ORGANISM: Human immunodeficiency virus type 1

<400> SEQUENCE: 150

Glu Thr Gly Gln Glu Thr Ala Tyr Phe Leu
1               5                   10

<210> SEQ ID NO 151
<211> LENGTH: 9
<212> TYPE: PRT
<213> ORGANISM: Human immunodeficiency virus type 1

<400> SEQUENCE: 151

Tyr Phe Leu Leu Lys Leu Ala Gly Arg
1               5

<210> SEQ ID NO 152
<211> LENGTH: 10
<212> TYPE: PRT
<213> ORGANISM: Human immunodeficiency virus type 1

<400> SEQUENCE: 152

Glu Thr Ala Tyr Phe Leu Leu Lys Leu Ala
1               5                   10

<210> SEQ ID NO 153
<211> LENGTH: 10
<212> TYPE: PRT
<213> ORGANISM: Human immunodeficiency virus type 1

<400> SEQUENCE: 153

Glu Thr Gly Gln Glu Thr Ala Tyr Phe Leu
1               5                   10

<210> SEQ ID NO 154
<211> LENGTH: 10
<212> TYPE: PRT
<213> ORGANISM: Human immunodeficiency virus type 1
```

<400> SEQUENCE: 154

Gln Glu Thr Ala Tyr Phe Leu Leu Lys Leu
1               5                   10

<210> SEQ ID NO 155
<211> LENGTH: 10
<212> TYPE: PRT
<213> ORGANISM: Human immunodeficiency virus type 1

<400> SEQUENCE: 155

Leu Glu Gly Lys Val Ile Leu Val Ala Val
1               5                   10

<210> SEQ ID NO 156
<211> LENGTH: 11
<212> TYPE: PRT
<213> ORGANISM: Human immunodeficiency virus type 1

<400> SEQUENCE: 156

Phe Leu Leu Lys Leu Ala Gly Arg Trp Pro Val
1               5                   10

<210> SEQ ID NO 157
<211> LENGTH: 11
<212> TYPE: PRT
<213> ORGANISM: Human immunodeficiency virus type 1

<400> SEQUENCE: 157

Lys Leu Ala Gly Arg Trp Pro Val Lys Thr Ile
1               5                   10

<210> SEQ ID NO 158
<211> LENGTH: 11
<212> TYPE: PRT
<213> ORGANISM: Human immunodeficiency virus type 1

<400> SEQUENCE: 158

His Val Ala Ser Gly Tyr Ile Glu Ala Glu Val
1               5                   10

<210> SEQ ID NO 159
<211> LENGTH: 11
<212> TYPE: PRT
<213> ORGANISM: Human immunodeficiency virus type 1

<400> SEQUENCE: 159

Leu Val Ala Val His Val Ala Ser Gly Tyr Ile
1               5                   10

<210> SEQ ID NO 160
<211> LENGTH: 11
<212> TYPE: PRT
<213> ORGANISM: Human immunodeficiency virus type 1

<400> SEQUENCE: 160

His Leu Glu Gly Lys Val Ile Leu Val Ala Val
1               5                   10

<210> SEQ ID NO 161
<211> LENGTH: 9
<212> TYPE: PRT
<213> ORGANISM: Human immunodeficiency virus type 1

<400> SEQUENCE: 161

Cys Thr Asn Val Ser Thr Val Gln Cys
1               5

-continued

<210> SEQ ID NO 162
<211> LENGTH: 10
<212> TYPE: PRT
<213> ORGANISM: Human immunodeficiency virus type 1

<400> SEQUENCE: 162

Pro Cys Thr Asn Val Ser Thr Val Gln Cys
1               5                   10

<210> SEQ ID NO 163
<211> LENGTH: 9
<212> TYPE: PRT
<213> ORGANISM: Human immunodeficiency virus type 1

<400> SEQUENCE: 163

Gly Pro Cys Thr Asn Val Ser Thr Val
1               5

<210> SEQ ID NO 164
<211> LENGTH: 9
<212> TYPE: PRT
<213> ORGANISM: Human immunodeficiency virus type 1

<400> SEQUENCE: 164

Asn Val Ser Thr Val Gln Cys Thr His
1               5

<210> SEQ ID NO 165
<211> LENGTH: 10
<212> TYPE: PRT
<213> ORGANISM: Human immunodeficiency virus type 1

<400> SEQUENCE: 165

Gly Thr Gly Pro Cys Thr Asn Val Ser Thr
1               5                   10

<210> SEQ ID NO 166
<211> LENGTH: 8
<212> TYPE: PRT
<213> ORGANISM: Human immunodeficiency virus type 1

<400> SEQUENCE: 166

Arg Ile Gln Arg Gly Pro Gly Arg
1               5

<210> SEQ ID NO 167
<211> LENGTH: 9
<212> TYPE: PRT
<213> ORGANISM: Human immunodeficiency virus type 1

<400> SEQUENCE: 167

Cys Thr Arg Pro Asn Asn Asn Thr Arg
1               5

<210> SEQ ID NO 168
<211> LENGTH: 9
<212> TYPE: PRT
<213> ORGANISM: Human immunodeficiency virus type 1

<400> SEQUENCE: 168

Ile Gln Arg Gly Pro Gly Arg Ala Phe
1               5

```
<210> SEQ ID NO 169
<211> LENGTH: 10
<212> TYPE: PRT
<213> ORGANISM: Human immunodeficiency virus type 1

<400> SEQUENCE: 169

Cys Thr Arg Pro Asn Asn Asn Thr Arg Lys
1               5                   10

<210> SEQ ID NO 170
<211> LENGTH: 10
<212> TYPE: PRT
<213> ORGANISM: Human immunodeficiency virus type 1

<400> SEQUENCE: 170

Arg Ile Arg Ile Gln Arg Gly Pro Gly Arg
1               5                   10

<210> SEQ ID NO 171
<211> LENGTH: 10
<212> TYPE: PRT
<213> ORGANISM: Human immunodeficiency virus type 1

<400> SEQUENCE: 171

Asn Thr Arg Lys Arg Ile Arg Ile Gln Arg
1               5                   10

<210> SEQ ID NO 172
<211> LENGTH: 10
<212> TYPE: PRT
<213> ORGANISM: Human immunodeficiency virus type 1

<400> SEQUENCE: 172

Arg Pro Asn Asn Asn Thr Arg Lys Arg Ile
1               5                   10

<210> SEQ ID NO 173
<211> LENGTH: 11
<212> TYPE: PRT
<213> ORGANISM: Human immunodeficiency virus type 1

<400> SEQUENCE: 173

Arg Ile Gln Arg Gly Pro Gly Arg Ala Phe Val
1               5                   10

<210> SEQ ID NO 174
<211> LENGTH: 15
<212> TYPE: PRT
<213> ORGANISM: Human immunodeficiency virus type 1

<400> SEQUENCE: 174

Arg Lys Arg Ile Arg Ile Gln Arg Gly Pro Gly Arg Ala Phe Val
1               5                   10                  15

<210> SEQ ID NO 175
<211> LENGTH: 9
<212> TYPE: PRT
<213> ORGANISM: Human immunodeficiency virus type 1

<400> SEQUENCE: 175

Ile Arg Ile Gln Arg Gly Pro Gly Arg
1               5

<210> SEQ ID NO 176
<211> LENGTH: 9
<212> TYPE: PRT
```

<210> SEQ ID NO 176
<211> LENGTH: 8
<212> TYPE: PRT
<213> ORGANISM: Human immunodeficiency virus type 1

<400> SEQUENCE: 176

Thr Arg Pro Asn Asn Asn Thr Arg Lys
1               5

<210> SEQ ID NO 177
<211> LENGTH: 9
<212> TYPE: PRT
<213> ORGANISM: Human immunodeficiency virus type 1

<400> SEQUENCE: 177

Gly Pro Gly Arg Ala Phe Val Thr Ile
1               5

<210> SEQ ID NO 178
<211> LENGTH: 10
<212> TYPE: PRT
<213> ORGANISM: Human immunodeficiency virus type 1

<400> SEQUENCE: 178

Arg Ile Arg Ile Gln Arg Gly Pro Gly Arg
1               5                   10

<210> SEQ ID NO 179
<211> LENGTH: 9
<212> TYPE: PRT
<213> ORGANISM: Human immunodeficiency virus type 1

<400> SEQUENCE: 179

Thr Arg Pro Asn Asn Asn Thr Arg Lys
1               5

<210> SEQ ID NO 180
<211> LENGTH: 9
<212> TYPE: PRT
<213> ORGANISM: Human immunodeficiency virus type 1

<400> SEQUENCE: 180

Gly Pro Gly Arg Ala Phe Val Thr Ile
1               5

<210> SEQ ID NO 181
<211> LENGTH: 10
<212> TYPE: PRT
<213> ORGANISM: Human immunodeficiency virus type 1

<400> SEQUENCE: 181

Arg Ile Gln Arg Gly Pro Gly Arg Ala Phe
1               5                   10

<210> SEQ ID NO 182
<211> LENGTH: 9
<212> TYPE: PRT
<213> ORGANISM: Human immunodeficiency virus type 1

<400> SEQUENCE: 182

Thr Arg Lys Arg Ile Arg Ile Gln Arg
1               5

<210> SEQ ID NO 183
<211> LENGTH: 9
<212> TYPE: PRT
<213> ORGANISM: Human immunodeficiency virus type 1

<400> SEQUENCE: 183

```
His Ser Phe Asn Cys Gly Gly Glu Phe
1               5

<210> SEQ ID NO 184
<211> LENGTH: 11
<212> TYPE: PRT
<213> ORGANISM: Human immunodeficiency virus type 1

<400> SEQUENCE: 184

Val Thr His Ser Phe Asn Cys Gly Gly Glu Phe
1               5                   10

<210> SEQ ID NO 185
<211> LENGTH: 10
<212> TYPE: PRT
<213> ORGANISM: Human immunodeficiency virus type 1

<400> SEQUENCE: 185

Trp Phe Asn Ser Thr Trp Ser Thr Glu Gly
1               5                   10

<210> SEQ ID NO 186
<211> LENGTH: 9
<212> TYPE: PRT
<213> ORGANISM: Human immunodeficiency virus type 1

<400> SEQUENCE: 186

Asn Ile Thr Gly Leu Leu Leu Thr Arg
1               5

<210> SEQ ID NO 187
<211> LENGTH: 9
<212> TYPE: PRT
<213> ORGANISM: Human immunodeficiency virus type 1

<400> SEQUENCE: 187

Ser Ser Asn Ile Thr Gly Leu Leu Leu
1               5

<210> SEQ ID NO 188
<211> LENGTH: 9
<212> TYPE: PRT
<213> ORGANISM: Human immunodeficiency virus type 1

<400> SEQUENCE: 188

Arg Cys Ser Ser Asn Ile Thr Gly Leu
1               5

<210> SEQ ID NO 189
<211> LENGTH: 9
<212> TYPE: PRT
<213> ORGANISM: Human immunodeficiency virus type 1

<400> SEQUENCE: 189

Ile Thr Gly Leu Leu Leu Thr Arg Asp
1               5

<210> SEQ ID NO 190
<211> LENGTH: 10
<212> TYPE: PRT
<213> ORGANISM: Human immunodeficiency virus type 1

<400> SEQUENCE: 190

Asn Ser Asn Asn Glu Ser Glu Ile Phe Arg
1               5                   10
```

<210> SEQ ID NO 191
<211> LENGTH: 11
<212> TYPE: PRT
<213> ORGANISM: Human immunodeficiency virus type 1

<400> SEQUENCE: 191

Ser Ser Asn Ile Thr Gly Leu Leu Leu Thr Arg
1               5                   10

<210> SEQ ID NO 192
<211> LENGTH: 10
<212> TYPE: PRT
<213> ORGANISM: Human immunodeficiency virus type 1

<400> SEQUENCE: 192

Gly Gly Asn Ser Asn Asn Glu Ser Glu Ile
1               5                   10

<210> SEQ ID NO 193
<211> LENGTH: 15
<212> TYPE: PRT
<213> ORGANISM: Human immunodeficiency virus type 1

<400> SEQUENCE: 193

Thr Gly Leu Leu Leu Thr Arg Asp Gly Gly Asn Ser Asn Asn Glu
1               5                   10                  15

<210> SEQ ID NO 194
<211> LENGTH: 8
<212> TYPE: PRT
<213> ORGANISM: Human immunodeficiency virus type 1

<400> SEQUENCE: 194

Ala Ala Ser Met Thr Leu Thr Val
1               5

<210> SEQ ID NO 195
<211> LENGTH: 8
<212> TYPE: PRT
<213> ORGANISM: Human immunodeficiency virus type 1

<400> SEQUENCE: 195

Ser Met Thr Leu Thr Val Gln Ala
1               5

<210> SEQ ID NO 196
<211> LENGTH: 8
<212> TYPE: PRT
<213> ORGANISM: Human immunodeficiency virus type 1

<400> SEQUENCE: 196

Met Thr Leu Thr Val Gln Ala Arg
1               5

<210> SEQ ID NO 197
<211> LENGTH: 8
<212> TYPE: PRT
<213> ORGANISM: Human immunodeficiency virus type 1

<400> SEQUENCE: 197

Met Gly Ala Ala Ser Met Thr Leu
1               5

<210> SEQ ID NO 198

-continued

```
<211> LENGTH: 8
<212> TYPE: PRT
<213> ORGANISM: Human immunodeficiency virus type 1

<400> SEQUENCE: 198

Ala Ala Ser Met Thr Leu Thr Val
1               5

<210> SEQ ID NO 199
<211> LENGTH: 9
<212> TYPE: PRT
<213> ORGANISM: Human immunodeficiency virus type 1

<400> SEQUENCE: 199

Thr Met Gly Ala Ala Ser Met Thr Leu
1               5

<210> SEQ ID NO 200
<211> LENGTH: 9
<212> TYPE: PRT
<213> ORGANISM: Human immunodeficiency virus type 1

<400> SEQUENCE: 200

Phe Leu Gly Ala Ala Gly Ser Thr Met
1               5

<210> SEQ ID NO 201
<211> LENGTH: 9
<212> TYPE: PRT
<213> ORGANISM: Human immunodeficiency virus type 1

<400> SEQUENCE: 201

Gly Ala Ala Ser Met Thr Leu Thr Val
1               5

<210> SEQ ID NO 202
<211> LENGTH: 9
<212> TYPE: PRT
<213> ORGANISM: Human immunodeficiency virus type 1

<400> SEQUENCE: 202

Ser Met Thr Leu Thr Val Gln Ala Arg
1               5

<210> SEQ ID NO 203
<211> LENGTH: 9
<212> TYPE: PRT
<213> ORGANISM: Human immunodeficiency virus type 1

<400> SEQUENCE: 203

Gly Ser Thr Met Gly Ala Ala Ser Met
1               5

<210> SEQ ID NO 204
<211> LENGTH: 9
<212> TYPE: PRT
<213> ORGANISM: Human immunodeficiency virus type 1

<400> SEQUENCE: 204

Leu Thr Val Gln Ala Arg Gln Leu Leu
1               5

<210> SEQ ID NO 205
<211> LENGTH: 9
<212> TYPE: PRT
<213> ORGANISM: Human immunodeficiency virus type 1
```

<400> SEQUENCE: 205

Ser Thr Met Gly Ala Ala Ser Met Thr
1               5

<210> SEQ ID NO 206
<211> LENGTH: 10
<212> TYPE: PRT
<213> ORGANISM: Human immunodeficiency virus type 1

<400> SEQUENCE: 206

Ser Thr Met Gly Ala Ala Ser Met Thr Leu
1               5                   10

<210> SEQ ID NO 207
<211> LENGTH: 10
<212> TYPE: PRT
<213> ORGANISM: Human immunodeficiency virus type 1

<400> SEQUENCE: 207

Val Gln Ala Arg Gln Leu Leu Ser Gly Ile
1               5                   10

<210> SEQ ID NO 208
<211> LENGTH: 10
<212> TYPE: PRT
<213> ORGANISM: Human immunodeficiency virus type 1

<400> SEQUENCE: 208

Thr Leu Thr Val Gln Ala Arg Gln Leu Leu
1               5                   10

<210> SEQ ID NO 209
<211> LENGTH: 10
<212> TYPE: PRT
<213> ORGANISM: Human immunodeficiency virus type 1

<400> SEQUENCE: 209

Ala Ser Met Thr Leu Thr Val Gln Ala Arg
1               5                   10

<210> SEQ ID NO 210
<211> LENGTH: 10
<212> TYPE: PRT
<213> ORGANISM: Human immunodeficiency virus type 1

<400> SEQUENCE: 210

Met Gly Ala Ala Ser Met Thr Leu Thr Val
1               5                   10

<210> SEQ ID NO 211
<211> LENGTH: 11
<212> TYPE: PRT
<213> ORGANISM: Human immunodeficiency virus type 1

<400> SEQUENCE: 211

Phe Leu Gly Ala Ala Gly Ser Thr Met Gly Ala
1               5                   10

<210> SEQ ID NO 212
<211> LENGTH: 11
<212> TYPE: PRT
<213> ORGANISM: Human immunodeficiency virus type 1

<400> SEQUENCE: 212

```
Thr Met Gly Ala Ala Ser Met Thr Leu Thr Val
1               5                   10

<210> SEQ ID NO 213
<211> LENGTH: 11
<212> TYPE: PRT
<213> ORGANISM: Human immunodeficiency virus type 1

<400> SEQUENCE: 213

Ser Met Thr Leu Thr Val Gln Ala Arg Gln Leu
1               5                   10

<210> SEQ ID NO 214
<211> LENGTH: 11
<212> TYPE: PRT
<213> ORGANISM: Human immunodeficiency virus type 1

<400> SEQUENCE: 214

Gly Ser Thr Met Gly Ala Ala Ser Met Thr Leu
1               5                   10

<210> SEQ ID NO 215
<211> LENGTH: 11
<212> TYPE: PRT
<213> ORGANISM: Human immunodeficiency virus type 1

<400> SEQUENCE: 215

Met Thr Leu Thr Val Gln Ala Arg Gln Leu Leu
1               5                   10

<210> SEQ ID NO 216
<211> LENGTH: 15
<212> TYPE: PRT
<213> ORGANISM: Human immunodeficiency virus type 1

<400> SEQUENCE: 216

Ser Met Thr Leu Thr Val Gln Ala Arg Gln Leu Leu Ser Gly Ile
1               5                   10                  15

<210> SEQ ID NO 217
<211> LENGTH: 15
<212> TYPE: PRT
<213> ORGANISM: Human immunodeficiency virus type 1

<400> SEQUENCE: 217

Gly Ala Ala Gly Ser Thr Met Gly Ala Ala Ser Met Thr Leu Thr
1               5                   10                  15

<210> SEQ ID NO 218
<211> LENGTH: 9
<212> TYPE: PRT
<213> ORGANISM: Human immunodeficiency virus type 1

<400> SEQUENCE: 218

Arg Gln Leu Leu Ser Gly Ile Val Gln
1               5

<210> SEQ ID NO 219
<211> LENGTH: 9
<212> TYPE: PRT
<213> ORGANISM: Human immunodeficiency virus type 1

<400> SEQUENCE: 219

Cys Thr Asn Val Ser Thr Val Gln Cys
1               5
```

<210> SEQ ID NO 220
<211> LENGTH: 45
<212> TYPE: PRT
<213> ORGANISM: Human immunodeficiency virus type 1

<400> SEQUENCE: 220

Tyr Cys Ala Pro Ala Gly Phe Ala Ile Leu Lys Cys Lys Asp Asn Lys
1               5                   10                  15

Phe Asn Gly Lys Gly Pro Cys Thr Asn Val Ser Thr Val Gln Cys Thr
            20                  25                  30

Cys Lys Asp Asn Lys Phe Asn Gly Lys Gly Pro Cys Thr
        35                  40                  45

<210> SEQ ID NO 221
<211> LENGTH: 14
<212> TYPE: PRT
<213> ORGANISM: Human immunodeficiency virus type 1

<400> SEQUENCE: 221

Lys Cys Lys Asp Asn Lys Phe Asn Gly Lys Gly Pro Cys Thr
1               5                   10

<210> SEQ ID NO 222
<211> LENGTH: 38
<212> TYPE: PRT
<213> ORGANISM: Human immunodeficiency virus type 1

<400> SEQUENCE: 222

Asn Cys Thr Arg Pro Asn Asn Asn Thr Arg Lys Arg Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn
        35

<210> SEQ ID NO 223
<211> LENGTH: 29
<212> TYPE: PRT
<213> ORGANISM: Human immunodeficiency virus type 1

<400> SEQUENCE: 223

Lys Cys Thr Asp Leu Lys Asn Asp Thr Asn Thr Asn Ser Ser Ser Gly
1               5                   10                  15

Arg Met Ile Met Glu Lys Gly Glu Ile Lys Asn Cys Ser
            20                  25

<210> SEQ ID NO 224
<211> LENGTH: 23
<212> TYPE: PRT
<213> ORGANISM: Human immunodeficiency virus type 1

<400> SEQUENCE: 224

Phe Cys Ala Ser Asp Ala Lys Ala Tyr Asp Thr Glu Val His Asn Val
1               5                   10                  15

Trp Ala Thr His Ala Cys Val
            20

<210> SEQ ID NO 225
<211> LENGTH: 36
<212> TYPE: PRT
<213> ORGANISM: Human immunodeficiency virus type 1

<400> SEQUENCE: 225

```
Tyr Cys Asn Ser Thr Gln Leu Phe Asn Ser Thr Trp Phe Asn Ser Thr
1               5                   10                  15

Trp Ser Thr Glu Gly Ser Asn Asn Thr Glu Gly Ser Asp Thr Ile Thr
            20                  25                  30

Leu Pro Cys Arg
        35
```

<210> SEQ ID NO 226
<211> LENGTH: 9
<212> TYPE: PRT
<213> ORGANISM: Human immunodeficiency virus type 1

<400> SEQUENCE: 226

```
Gly Cys Ser Gly Lys Leu Ile Cys Thr
1               5
```

<210> SEQ ID NO 227
<211> LENGTH: 12
<212> TYPE: PRT
<213> ORGANISM: Human immunodeficiency virus type 1

<400> SEQUENCE: 227

```
Lys Cys Asp Tyr Pro Glu Trp Gln Trp Leu Cys Thr
1               5                   10
```

<210> SEQ ID NO 228
<211> LENGTH: 18
<212> TYPE: PRT
<213> ORGANISM: Human immunodeficiency virus type 1

<400> SEQUENCE: 228

```
Arg Arg Trp Cys Phe Arg Val Cys Tyr Arg Gly Phe Cys Tyr Arg Lys
1               5                   10                  15

Cys Arg
```

<210> SEQ ID NO 229
<211> LENGTH: 18
<212> TYPE: PRT
<213> ORGANISM: Human immunodeficiency virus type 1

<400> SEQUENCE: 229

```
Gly Ile Cys Arg Cys Ile Cys Gly Arg Gly Ile Cys Arg Cys Ile Cys
1               5                   10                  15

Gly Lys
```

<210> SEQ ID NO 230
<211> LENGTH: 17
<212> TYPE: PRT
<213> ORGANISM: Human immunodeficiency virus type 1

<400> SEQUENCE: 230

```
Lys Gly Cys Arg Cys Ile Cys Gly Arg Gly Ile Cys Arg Cys Ile Cys
1               5                   10                  15

Gly
```

<210> SEQ ID NO 231
<211> LENGTH: 7
<212> TYPE: PRT
<213> ORGANISM: Human immunodeficiency virus type 1

<400> SEQUENCE: 231

```
Gln Cys Ser Val Thr Cys Gly
```

-continued 1 5

<210> SEQ ID NO 232
<211> LENGTH: 17
<212> TYPE: PRT
<213> ORGANISM: Human immunodeficiency virus type 1

<400> SEQUENCE: 232

Lys Trp Cys Phe Arg Val Cys Tyr Arg Gly Ile Cys Tyr Arg Arg Cys
1 5 10 15

Arg

<210> SEQ ID NO 233
<211> LENGTH: 18
<212> TYPE: PRT
<213> ORGANISM: Human immunodeficiency virus type 1

<400> SEQUENCE: 233

Arg Cys Leu Cys Arg Arg Gly Val Cys Arg Cys Leu Cys Arg Arg Gly
1 5 10 15

Val Cys

<210> SEQ ID NO 234
<211> LENGTH: 20
<212> TYPE: PRT
<213> ORGANISM: Human immunodeficiency virus type 1

<400> SEQUENCE: 234

Cys Leu Gly Ile Gly Ser Cys Asn Asp Phe Ala Gly Cys Gly Tyr Ala
1 5 10 15

Val Val Cys Lys
20

<210> SEQ ID NO 235
<211> LENGTH: 13
<212> TYPE: PRT
<213> ORGANISM: Human immunodeficiency virus type 1

<400> SEQUENCE: 235

Tyr Pro Ile Val Gln Asn Ile Gln Gly Gln Met Val His
1 5 10

<210> SEQ ID NO 236
<211> LENGTH: 19
<212> TYPE: PRT
<213> ORGANISM: Human immunodeficiency virus type 1

<400> SEQUENCE: 236

Tyr Lys Arg Trp Ile Ile Leu Gly Leu Asn Lys Ile Val Arg Met Tyr
1 5 10 15

Ser Pro Thr

<210> SEQ ID NO 237
<211> LENGTH: 38
<212> TYPE: PRT
<213> ORGANISM: Human immunodeficiency virus type 1

<400> SEQUENCE: 237

Glu Gln Thr Arg Ala Asn Ser Pro Thr Arg Arg Glu Leu Gln Val Trp
1 5 10 15

Gly Arg Asp Asn Asn Ser Pro Ser Glu Ala Gly Ala Asp Arg Gln Gly
20 25 30

-continued

Thr Val Ser Phe Asn Phe
        35

<210> SEQ ID NO 238
<211> LENGTH: 52
<212> TYPE: PRT
<213> ORGANISM: Human immunodeficiency virus type 1

<400> SEQUENCE: 238

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly
    50

<210> SEQ ID NO 239
<211> LENGTH: 28
<212> TYPE: PRT
<213> ORGANISM: Human immunodeficiency virus type 1

<400> SEQUENCE: 239

Val Lys Leu Trp Tyr Gln Leu Glu Lys Glu Pro Ile Val Gly Ala Glu
1               5                   10                  15

Thr Phe Tyr Val Asp Gly Ala Ala Asn Arg Glu Thr
            20                  25

<210> SEQ ID NO 240
<211> LENGTH: 54
<212> TYPE: PRT
<213> ORGANISM: Human immunodeficiency virus type 1

<400> SEQUENCE: 240

His Leu Glu Gly Lys Val Ile Leu Val Ala Val His Val Ala Ser Gly
1               5                   10                  15

Tyr Ile Glu Ala Glu Val Ile Pro Ala Glu Thr Gly Gln Glu Thr Ala
            20                  25                  30

Tyr Phe Leu Leu Lys Leu Ala Gly Arg Trp Pro Val Lys Thr Ile His
        35                  40                  45

Thr Asp Asn Gly Ser Asn
    50

<210> SEQ ID NO 241
<211> LENGTH: 15
<212> TYPE: PRT
<213> ORGANISM: Human immunodeficiency virus type 1

<400> SEQUENCE: 241

Phe Lys Arg Lys Gly Gly Ile Gly Gly Tyr Ser Ala Gly Glu Arg
1               5                   10                  15

<210> SEQ ID NO 242
<211> LENGTH: 13
<212> TYPE: PRT
<213> ORGANISM: Human immunodeficiency virus type 1

<400> SEQUENCE: 242

Pro His Pro Arg Ile Ser Ser Glu Val His Ile Pro Leu
1               5                   10

```
<210> SEQ ID NO 243
<211> LENGTH: 18
<212> TYPE: PRT
<213> ORGANISM: Human immunodeficiency virus type 1

<400> SEQUENCE: 243

Gly Val Ser Ile Glu Trp Arg Lys Lys Arg Tyr Ser Thr Gln Val Asp
1               5                   10                  15

Pro Glu

<210> SEQ ID NO 244
<211> LENGTH: 27
<212> TYPE: PRT
<213> ORGANISM: Human immunodeficiency virus type 1

<400> SEQUENCE: 244

Ile His Phe Arg Ile Gly Cys Arg His Ser Arg Ile Gly Val Thr Arg
1               5                   10                  15

Gln Arg Arg Ala Arg Asn Gly Ala Ser Arg Ser
            20                  25

<210> SEQ ID NO 245
<211> LENGTH: 12
<212> TYPE: PRT
<213> ORGANISM: Human immunodeficiency virus type 1

<400> SEQUENCE: 245

Phe Ile Thr Lys Ala Leu Gly Ile Ser Tyr Gly Arg
1               5                   10

<210> SEQ ID NO 246
<211> LENGTH: 16
<212> TYPE: PRT
<213> ORGANISM: Human immunodeficiency virus type 1

<400> SEQUENCE: 246

Gly Thr Gly Pro Cys Thr Asn Val Ser Thr Val Gln Cys Thr His Gly
1               5                   10                  15

<210> SEQ ID NO 247
<211> LENGTH: 26
<212> TYPE: PRT
<213> ORGANISM: Human immunodeficiency virus type 1

<400> SEQUENCE: 247

Asn Cys Thr Arg Pro Asn Asn Asn Thr Arg Lys Arg Ile Arg Ile Gln
1               5                   10                  15

Arg Gly Pro Gly Arg Ala Phe Val Thr Ile
            20                  25

<210> SEQ ID NO 248
<211> LENGTH: 12
<212> TYPE: PRT
<213> ORGANISM: Human immunodeficiency virus type 1

<400> SEQUENCE: 248

Ile Val Thr His Ser Phe Asn Cys Gly Gly Glu Phe
1               5                   10

<210> SEQ ID NO 249
<211> LENGTH: 26
<212> TYPE: PRT
<213> ORGANISM: Human immunodeficiency virus type 1

<400> SEQUENCE: 249
```

```
Arg Cys Ser Ser Asn Ile Thr Gly Leu Leu Leu Thr Arg Asp Gly Gly
1               5                   10                  15

Asn Ser Asn Asn Glu Ser Glu Ile Phe Arg
                20                  25

<210> SEQ ID NO 250
<211> LENGTH: 29
<212> TYPE: PRT
<213> ORGANISM: Human immunodeficiency virus type 1

<400> SEQUENCE: 250

Leu Gly Phe Leu Gly Ala Ala Gly Ser Thr Met Gly Ala Ala Ser Met
1               5                   10                  15

Thr Leu Thr Val Gln Ala Arg Gln Leu Leu Ser Gly Ile
                20                  25

<210> SEQ ID NO 251
<211> LENGTH: 11
<212> TYPE: PRT
<213> ORGANISM: Human immunodeficiency virus type 1

<400> SEQUENCE: 251

Gln Arg Arg Gln Asp Ile Leu Asp Leu Trp Ile
1               5                   10

<210> SEQ ID NO 252
<211> LENGTH: 9
<212> TYPE: PRT
<213> ORGANISM: Human immunodeficiency virus type 1

<400> SEQUENCE: 252

Gln Ala Arg Gln Leu Leu Ser Gly Ile
1               5

<210> SEQ ID NO 253
<211> LENGTH: 9
<212> TYPE: PRT
<213> ORGANISM: Human immunodeficiency virus type 1

<400> SEQUENCE: 253

Arg Gln Leu Leu Ser Gly Ile Val Gln
1               5

<210> SEQ ID NO 254
<211> LENGTH: 29
<212> TYPE: PRT
<213> ORGANISM: Human immunodeficiency virus type 1

<400> SEQUENCE: 254

Leu Gly Phe Leu Gly Ala Ala Gly Ser Thr Met Gly Ala Ala Ser Met
1               5                   10                  15

Thr Leu Thr Val Gln Ala Arg Gln Leu Leu Ser Gly Ile
                20                  25

<210> SEQ ID NO 255
<211> LENGTH: 9
<212> TYPE: PRT
<213> ORGANISM: Human immunodeficiency virus type 1

<400> SEQUENCE: 255

Asn Ile Thr Gly Leu Leu Leu Thr Arg
1               5
```

-continued

```
<210> SEQ ID NO 256
<211> LENGTH: 11
<212> TYPE: PRT
<213> ORGANISM: Human immunodeficiency virus type 1

<400> SEQUENCE: 256

Gln Arg Gly Pro Gly Arg Ala Phe Val Thr Ile
1               5                   10

<210> SEQ ID NO 257
<211> LENGTH: 12
<212> TYPE: PRT
<213> ORGANISM: Human immunodeficiency virus type 1

<400> SEQUENCE: 257

Phe Ile Thr Lys Ala Leu Gly Ile Ser Tyr Gly Arg
1               5                   10

<210> SEQ ID NO 258
<211> LENGTH: 19
<212> TYPE: PRT
<213> ORGANISM: Human immunodeficiency virus type 1

<400> SEQUENCE: 258

His Leu Glu Gly Lys Val Ile Leu Val Ala Val His Val Ala Ser Gly
1               5                   10                  15

Tyr Ile Glu

<210> SEQ ID NO 259
<211> LENGTH: 19
<212> TYPE: PRT
<213> ORGANISM: Human immunodeficiency virus type 1

<400> SEQUENCE: 259

Thr Ala Tyr Phe Leu Leu Lys Leu Ala Gly Arg Trp Pro Val Lys Thr
1               5                   10                  15

Ile His Thr

<210> SEQ ID NO 260
<211> LENGTH: 13
<212> TYPE: PRT
<213> ORGANISM: Human immunodeficiency virus type 1

<400> SEQUENCE: 260

Gln Val Thr Leu Trp Gln Arg Pro Leu Val Thr Ile Lys
1               5                   10

<210> SEQ ID NO 261
<211> LENGTH: 8
<212> TYPE: PRT
<213> ORGANISM: Human immunodeficiency virus type 1

<400> SEQUENCE: 261

Ser Gln Glu Val Lys Asn Trp Met
1               5

<210> SEQ ID NO 262
<211> LENGTH: 15
<212> TYPE: PRT
<213> ORGANISM: Human immunodeficiency virus type 1

<400> SEQUENCE: 262

Arg Trp Ile Ile Leu Gly Leu Asn Lys Ile Val Arg Met Tyr Ser
1               5                   10                  15
```

<210> SEQ ID NO 263
<211> LENGTH: 13
<212> TYPE: PRT
<213> ORGANISM: Human immunodeficiency virus type 1

<400> SEQUENCE: 263

Tyr Pro Ile Val Gln Asn Ile Gln Gly Gln Met Val His
1               5                   10

<210> SEQ ID NO 264
<211> LENGTH: 13
<212> TYPE: PRT
<213> ORGANISM: Human immunodeficiency virus type 1

<400> SEQUENCE: 264

Phe Lys Arg Ile Val Gln Arg Ile Lys Asp Phe Leu Arg
1               5                   10

<210> SEQ ID NO 265
<211> LENGTH: 13
<212> TYPE: PRT
<213> ORGANISM: Human immunodeficiency virus type 1

<400> SEQUENCE: 265

Tyr Gly Leu Ala Lys Ala Arg Gln Ala Arg Leu Ala His
1               5                   10

<210> SEQ ID NO 266
<211> LENGTH: 6
<212> TYPE: PRT
<213> ORGANISM: Human immunodeficiency virus type 1

<400> SEQUENCE: 266

Met Gly Ala Arg Ala Ser
1               5

<210> SEQ ID NO 267
<211> LENGTH: 5
<212> TYPE: PRT
<213> ORGANISM: Human immunodeficiency virus type 1

<400> SEQUENCE: 267

Glu Lys Ile Arg Leu
1               5

<210> SEQ ID NO 268
<211> LENGTH: 6
<212> TYPE: PRT
<213> ORGANISM: Human immunodeficiency virus type 1

<400> SEQUENCE: 268

Ala Leu Gly Pro Ala Ala
1               5

<210> SEQ ID NO 269
<211> LENGTH: 5
<212> TYPE: PRT
<213> ORGANISM: Human immunodeficiency virus type 1

<400> SEQUENCE: 269

Thr Glu Arg Gln Ala
1               5

<210> SEQ ID NO 270
<211> LENGTH: 5

```
<212> TYPE: PRT
<213> ORGANISM: Human immunodeficiency virus type 1

<400> SEQUENCE: 270

Thr Thr Pro Pro Gln
1               5

<210> SEQ ID NO 271
<211> LENGTH: 5
<212> TYPE: PRT
<213> ORGANISM: Human immunodeficiency virus type 1

<400> SEQUENCE: 271

Ala Glu Ala Met Ser
1               5

<210> SEQ ID NO 272
<211> LENGTH: 6
<212> TYPE: PRT
<213> ORGANISM: Human immunodeficiency virus type 1

<400> SEQUENCE: 272

Pro Ala Ile Phe Gln Ser
1               5

<210> SEQ ID NO 273
<211> LENGTH: 5
<212> TYPE: PRT
<213> ORGANISM: Human immunodeficiency virus type 1

<400> SEQUENCE: 273

Asp Lys Lys His Gln
1               5

<210> SEQ ID NO 274
<211> LENGTH: 7
<212> TYPE: PRT
<213> ORGANISM: Human immunodeficiency virus type 1

<400> SEQUENCE: 274

Cys Leu Val Thr Lys Lys Cys
1               5

<210> SEQ ID NO 275
<211> LENGTH: 6
<212> TYPE: PRT
<213> ORGANISM: Human immunodeficiency virus type 1

<400> SEQUENCE: 275

Cys Lys Ile Thr Gly Cys
1               5

<210> SEQ ID NO 276
<211> LENGTH: 7
<212> TYPE: PRT
<213> ORGANISM: Human immunodeficiency virus type 1

<400> SEQUENCE: 276

Glu Lys Tyr His Ser Asn Trp
1               5

<210> SEQ ID NO 277
<211> LENGTH: 4
<212> TYPE: PRT
<213> ORGANISM: Human immunodeficiency virus type 1
```

```
<400> SEQUENCE: 277

Met Glu Pro Val
1

<210> SEQ ID NO 278
<211> LENGTH: 6
<212> TYPE: PRT
<213> ORGANISM: Human immunodeficiency virus type 1

<400> SEQUENCE: 278

Val Ala Ile Val Ala Leu
1               5

<210> SEQ ID NO 279
<211> LENGTH: 6
<212> TYPE: PRT
<213> ORGANISM: Human immunodeficiency virus type 1

<400> SEQUENCE: 279

Trp Asp Val Asp Asp Leu
1               5

<210> SEQ ID NO 280
<211> LENGTH: 6
<212> TYPE: PRT
<213> ORGANISM: Human immunodeficiency virus type 1

<400> SEQUENCE: 280

Met Arg Val Lys Glu Lys
1               5

<210> SEQ ID NO 281
<211> LENGTH: 6
<212> TYPE: PRT
<213> ORGANISM: Human immunodeficiency virus type 1

<400> SEQUENCE: 281

Thr Val Trp Gly Ile Lys
1               5

<210> SEQ ID NO 282
<211> LENGTH: 6
<212> TYPE: PRT
<213> ORGANISM: Human immunodeficiency virus type 1

<400> SEQUENCE: 282

Arg Ile Val Glu Leu Leu
1               5

<210> SEQ ID NO 283
<211> LENGTH: 6
<212> TYPE: PRT
<213> ORGANISM: Human immunodeficiency virus type 1

<400> SEQUENCE: 283

Thr Asn Ala Ala Cys Ala
1               5

<210> SEQ ID NO 284
<211> LENGTH: 21
<212> TYPE: PRT
<213> ORGANISM: Human immunodeficiency virus type 1

<400> SEQUENCE: 284

Cys Lys Thr Ile Leu Lys Ala Leu Gly Pro Ala Ala Thr Leu Glu Glu
```

```
                 1               5              10              15

Met Met Thr Ala Cys
                20
```

<210> SEQ ID NO 285
<211> LENGTH: 5
<212> TYPE: PRT
<213> ORGANISM: Human immunodeficiency virus type 1

<400> SEQUENCE: 285

```
Gly Cys Trp Lys Cys
1               5
```

<210> SEQ ID NO 286
<211> LENGTH: 31
<212> TYPE: PRT
<213> ORGANISM: Human immunodeficiency virus type 1

<400> SEQUENCE: 286

```
Ser Glu Cys Gly His Lys Ala Ile Gly Thr Val Leu Val Gly Pro Thr
1               5                  10                  15

Pro Val Asn Ile Ile Gly Arg Asn Leu Leu Thr Gln Ile Gly Cys
            20                  25                  30
```

<210> SEQ ID NO 287
<211> LENGTH: 4
<212> TYPE: PRT
<213> ORGANISM: Human immunodeficiency virus type 1

<400> SEQUENCE: 287

```
Cys Asp Lys Cys
1
```

<210> SEQ ID NO 288
<211> LENGTH: 10
<212> TYPE: PRT
<213> ORGANISM: Human immunodeficiency virus type 1

<400> SEQUENCE: 288

```
Cys Ser Pro Gly Ile Trp Gln Leu Asp Cys
1               5                  10
```

<210> SEQ ID NO 289
<211> LENGTH: 20
<212> TYPE: PRT
<213> ORGANISM: Human immunodeficiency virus type 1

<400> SEQUENCE: 289

```
Cys Phe Ser Asp Ser Ala Ile Arg Lys Ala Leu Leu Gly His Ile Val
1               5                  10                  15

Ser Pro Arg Cys
            20
```

<210> SEQ ID NO 290
<211> LENGTH: 16
<212> TYPE: PRT
<213> ORGANISM: Human immunodeficiency virus type 1

<400> SEQUENCE: 290

```
Cys Thr Asn Cys Tyr Cys Lys Lys Cys Cys Phe His Cys Gln Val Cys
1               5                  10                  15
```

<210> SEQ ID NO 291
<211> LENGTH: 5

```
<212> TYPE: PRT
<213> ORGANISM: Human immunodeficiency virus type 1

<400> SEQUENCE: 291

Cys Arg Gly Asp Cys
1               5

<210> SEQ ID NO 292
<211> LENGTH: 6
<212> TYPE: PRT
<213> ORGANISM: Human immunodeficiency virus type 1

<400> SEQUENCE: 292

Cys Asn Glu Asp Cys Gly
1               5

<210> SEQ ID NO 293
<211> LENGTH: 21
<212> TYPE: PRT
<213> ORGANISM: Human immunodeficiency virus type 1

<400> SEQUENCE: 293

Cys Ala Ser Asp Ala Lys Ala Tyr Asp Thr Glu Val His Asn Val Trp
1               5                   10                  15

Ala Thr His Ala Cys
            20

<210> SEQ ID NO 294
<211> LENGTH: 30
<212> TYPE: PRT
<213> ORGANISM: Human immunodeficiency virus type 1

<400> SEQUENCE: 294

Cys Ala Pro Ala Gly Phe Ala Ile Leu Lys Cys Asn Asn Lys Thr Phe
1               5                   10                  15

Asn Gly Thr Gly Pro Cys Thr Asn Val Ser Thr Val Gln Cys
            20                  25                  30

<210> SEQ ID NO 295
<211> LENGTH: 12
<212> TYPE: PRT
<213> ORGANISM: Human immunodeficiency virus type 1

<400> SEQUENCE: 295

Cys Asn Asn Lys Thr Phe Asn Gly Thr Gly Pro Cys
1               5                   10

<210> SEQ ID NO 296
<211> LENGTH: 9
<212> TYPE: PRT
<213> ORGANISM: Human immunodeficiency virus type 1

<400> SEQUENCE: 296

Cys Thr Asn Val Ser Thr Val Gln Cys
1               5

<210> SEQ ID NO 297
<211> LENGTH: 7
<212> TYPE: PRT
<213> ORGANISM: Human immunodeficiency virus type 1

<400> SEQUENCE: 297

Cys Ser Gly Lys Leu Ile Cys
1               5
```

```
<210> SEQ ID NO 298
<211> LENGTH: 13
<212> TYPE: PRT
<213> ORGANISM: Human immunodeficiency virus type 1

<400> SEQUENCE: 298

Trp Lys Lys Ile Arg Arg Phe Val Ser Gln Val Ile Met
1               5                   10
```

STEREOISOMER PEPTIDES AND THEIR POLYMER CONJUGATES FOR HIV DISEASE

CROSS-REFERENCE TO RELATED APPLICATIONS

This application claims the benefit of U.S. Provisional Application No. 61/213,345, filed on Jul. 14, 2009 and U.S. Provisional Application No. 61/213,548 filed Jul. 18, 2009. The above applications are hereby incorporated herein by reference.

STATEMENT REGARDING FEDERALLY SPONSORED RESEARCH OR DEVELOPMENT

There are no Federal rights in this invention

SEQUENCE LISTING

The present utility application hereby incorporates by reference, in its entirety, the Sequence Listing containing amino acid sequences SEQ. ID NOs. 1 through 298, in a file labeled: "SEQUENCE LISTING (TEXT FILE).txt"

FIELD OF INVENTION

This invention relates to peptides and their polymer conjugates, and uses thereof in the treatment of HIV disease.

BACKGROUND OF THE INVENTION

HIV remains a global health problem of unprecedented dimensions. Globally, there are about 35 Million people living with HIV, about 25 Million have died, and approximately 3.0 Million new HIV infections occur worldwide annually. In the US 60,000 new cases occur annually.

Human immunodeficiency virus (HIV-1) is a retrovirus that leads to AIDS, a condition in humans in which the immune system begins to fail, leading to life-threatening opportunistic infections. HIV-1 enters macrophages and CD4+T cells by interaction of glycoproteins on its surface to receptors on the target cell followed by fusion of the viral envelope with the cell membrane and the release of the HIV capsid into the cell. HIV entry into human cells requires the interaction of several key proteins. It is initiated by binding of the HIV envelope surface glycoprotein subunit gp120 to the cellular receptor CD4, found on the surface of helper T cells in the human immune system, and a chemokine co-receptor, generally CCR5 or CXCR4, which is essential for HIV-1 infection. The binding of gp120 to CD4 causes a conformational change in gp120 allowing fusion of the membranes and subsequent entry of the viral core into the host cell. Thus blocking of the conformational change in gp41 that is crucial for fusion should inhibit viral entry into host cells.

Attempts to produce traditional vaccines have been unsuccessful. Although different non-traditional approaches to develop a vaccine are emerging, the prospect of generating a functional vaccine to control infection and spread of HIV is still many years away. Hence, there exists a need to create a therapeutic HIV vaccine to achieve long term remission without treatment or complete eradication of persistent virus and achievement of a full cure for HIV infection and AIDS.

Given the lack of efficacy of anti-HIV vaccines, and the lack of stability, bioavailability, low potency, toxicity problems, and the inability to kill the virus by the HIV-1 inhibitors developed so far, there is, accordingly, the need for developing novel compounds with a delivery system that is non-toxic, inert, water-soluble, stable, and biocompatible. Similarly, the compounds should be target specific, and have enhanced stability, higher potency, with minimal or no toxicity, and potentially capable to raise an immune response.

SUMMARY OF THE INVENTION

This invention comprises a group of peptides, composed of essentially linear and cyclic peptides mimicking specific sequences identified from the domains of HIV-1 proteins. These peptides are synthesized with both D- and L-amino acids and all D-amino acids, and thus they are stereoisomer peptides which are stable and have extended shelf-life; they are resistant to degradation by hydrolysis and have longer half-life in blood circulation. These enhanced properties provide potential for oral bioavailability, and can be used in harsh mucosal environments to prevent and treat HIV infections. The compounds disclosed in this invention are very different to all the molecules described so far and constitute the next generation of bio-therapeutics for the anti-HIV strategies described here.

One aspect of the invention relates to conjugation of the single and/or multi-stereoisomer peptide(s) with water-soluble polymer and the use of those conjugates as specific intracellular carriers of the stereoisomer peptides into cells (e.g., CD4+ cells, macrophages, epithelial and among others) to prevent HIV-1 entry into the cells. The peptides target specific functional domains of HIV proteins and therefore they are expected to function as competitive antagonists, ligands or blockers of HIV-1 fusion and replication, preventing and/or inhibiting the entry of the virus into the host cell; hence their potential as therapeutic compounds for the treatment of HIV/AIDS.

Specifically the invention discloses two hundred and ninety eight (298) peptides with sequences labeled SEQ ID NO: 1 through SEQ ID NO: 298; disclosed in the file 'SEQUENCE LISTING (TEXT FILE).TXT' These peptides were identified following a strategy based on the use of scientific knowledge, advanced technologies, innovative ideas, and a variety of software and bioinformatics tools, and comparison and prediction algorithms.

HIV protein sequence databases were used to identify the peptides and their selection was guided by the molecular structure properties, the three-dimensional (3D) structure of the target HIV-1 proteins, and related scientific information. One approach consisted in selecting peptide sequences that are not homologous to human protein sequences. These particular sequences were then analyzed using prediction algorithms based on HLA-binding motifs and peptide specific T cells to determine their immunogenic potential. In this way, only peptide sequences with strong-T cell epitopes that bind MHC-1 (major histocompatibility complex class I) molecules were selected. These peptides comprise a set of 218 short sequences. A second approach consisted in analyzing regions and domains of the HIV-1 proteins that are known to be important for viral replication, function, and survival. Sequences comprising such important domains were analyzed with a variety of software and bioinformatics tools to determine their overall alpha-helix, beta-sheet or cyclic structures including their net positive charge, hydrophobic amino acid content, isoelectric point, molecular weight, and other physicochemical parameters. These properties were used to select the actual number of amino acids in the sequence of the peptide.

Sequences containing Cys residues in the HIV protein domains of interest were also selected since they can form cyclic peptides by disulfide bridge formation via oxidation of the Cys residues; the number of Cys residues in the peptide determines the rigidity of the cyclic structure. The 3D structure of HIV-1 proteins was also analyzed to identify key sites or domains that are involved in viral function including but not limited to protein-protein interactions, protein folding loops that maintain stability, and substrate and ion interaction sites, to name a few. Since all the peptides selected mimic the natural sequences of the target proteins they are expected to function as competitive ligands or blockers potentially disrupting proteins important for replication, function, and survival of the virus. The targeted HIV-1 proteins include nef, gp160 which includes gp120 and gp41, tat, integrase, protease, gag p24, p17, p2p7p1p6, vpu and reverse transcriptase.

This invention further relates to the creation of novel stereoisomer compounds and their polymer conjugates which was based on innovative ideas and the use of available scientific knowledge on the physicochemical properties of amino acids including but not limited to their chemical configuration and chirality, enantiomeric forms, chemical modifications, as well as the extensive knowledge available on the properties of biodegradable and biocompatible polymers and their use as carriers for delivery of a variety of molecules. All this knowledge crosses the boundaries of many scientific fields and was put together to create novel stereoisomer peptide compounds, novel stereoisomer-peptide-polymer conjugate compounds and novel multi-stereoisomer peptide-polymer compounds which constitute the subject matter of this invention.

In one aspect, this invention relates to peptides with alpha-helix, beta-sheet or cyclic structures. The cyclic peptides may have 2 or 4 or 6 Cys residues that form single, double, or triple disulfide bonds, respectively, via oxidation, creating constrained cyclic structures.

In another aspect, this invention discloses a group of 30 peptides from the group of 298 peptides that contain Cys residues on their sequences and that can form disulfide bonds via chemical oxidation. These peptides are aimed to the hydrophobic cavity created by the six-helix bundle formation of the NHR and CHR regions of the HIV gp160 envelope glycoprotein to disrupt the entry and fusion of the virus into the host cell.

In still another aspect, this invention discloses a group of 16 peptides from the group of 298 peptides that mimic each a corresponding short domain of a major HIV protein. These peptides do not overlap with human protein sequences based on their comparisons with human proteins using a BLAST algorithm. The sequences identified were then analyzed with prediction algorithms to deduce strong T-cell epitopes that bind MHC with potential immunogenic properties.

In yet another aspect, this invention discloses 15 peptides from the group of 298 peptides with linear alpha-helix structure which is formed by the aliphatic and aromatic hydrocarbon side chains of hydrophobic amino acids which have potential to block each a corresponding domain of an HIV-1 protein disrupting protein-protein interactions, protein folding loops, and viral functional domains.

In a particular aspect, one peptide from the group of 298 peptides mimics the Tat HIV transduction domain. The sequence of the peptide was modified to strengthen the alpha-helical content, to enhance the transduction potential compared with the native Tat sequence. The structure of this peptide resemble a microbial peptide and thus is a cell penetrating peptide that can be attached to a non-degradable linker to a particular polymer to aid the delivery of other peptides to tissues, cell and sub-cellular locations. An additional set of 18 peptides have short sequences targeting each the corresponding short domain of a major HIV-1 protein.

In a particular aspect, this invention discloses one peptide from the group of 298 peptides which have liner alpha-helix structure and which also resembles an antimicrobial peptide. This peptide mimics a domain of human lens ephithelium derived growth factor and given its affinity for HIV integrase it functions as a competitive ligand. This cell penetrating peptide (CPP) can be used as peptide ligand attached to a polymer carrier to enhance the delivery of other peptides of this invention to tissues, cells, and sub-cellular locations.

The invention also relates to particular methods for preparing the peptides, preferably peptides that are synthesized as stereoisomer peptides in their chiral forms containing mixtures of D- and L-amino acids or only D-amino acids to create D-peptides, and with acetylated and amidated ends; being the D-peptides the preferred compounds of this invention. These modifications result in stereoisomer peptides with enhanced physicochemical properties including higher stability and solubility in water, and resistance to degradation by enzymes present in human fluids.

This invention further refers to the preparation of peptide-polymer conjugate compounds in which linear and/or cyclic stereoisomer peptides are coupled to separate branches of a polymer via biodegradable linkers comprising two, three, or four amino acids, preferably selected from the amino acids Lys, Gly, Leu, and Phe by addition or substitution. The sequence of the di-, tri-, or tetra-oligopeptide will determine the biodegradability of the linker.

In certain aspects of this invention, a plural of peptides are selected from the set of 298 peptides, synthesized as D-peptides with modified ends, and conjugated each independently via a linker to a functional group of a branch of a polymer, which may be a biocompatible polymer such as N-(2-Hydroxypropyl) methacrylamide (HPMA). Poly HPMA is a linear scaffold polymer carrier with separate branches where individual molecules can be conjugated to functional groups of a linker attached to the polymer branch to create polymer conjugate compounds that are delivered by the polymer to tissues, cells and sub-cellular locations, and preferably using a peptide-ligand. The conjugates are created by coupling stereoisomer peptides via a biodegradable linker, and a peptide-ligand via a non-degradable linker. Preferred polymers for use with the present invention are activated HPMA copolymers synthesized via p-nitrophenyl ester aminolysis of the polymeric precursor.

The creation of the multi-targeted polymer conjugate will depend on the actual number of synthetic stereoisomer peptides that are conjugated each to a separate branch of the polymer to create the multi stereoisomer peptide-polymer conjugate compounds by copolymerization of monomers carrying each a different stereoisomer peptide coupled to a linker. The molecular weight of the polymer is preferably in the range of 15 to 45 kDa. The polymer carrier is expected to improve the physicochemical and pharmacokinetic properties of the polymer-drug conjugates by increasing circulating half-life, increasing the solubility of hydrophobic drugs, decrease drug toxicity, and potentially evade multidrug resistance.

The invention further provides pharmaceutical compositions for the stereoisomer peptide compounds, the stereoisomer peptide-polymer conjugate compound and the multi stereoisomer peptide-polymer conjugate compounds that may be prepared for administration by oral, transmucosal, parenteral (iv), transdermal and topical, and may be formulated in dosage forms appropriate for each route of administration using pharmaceutically acceptable excipients.

Other aspects and advantages of the invention will be apparent from the following description and the appended claims.

DETAILED DESCRIPTION OF THE INVENTION

Definitions

Figure 1:
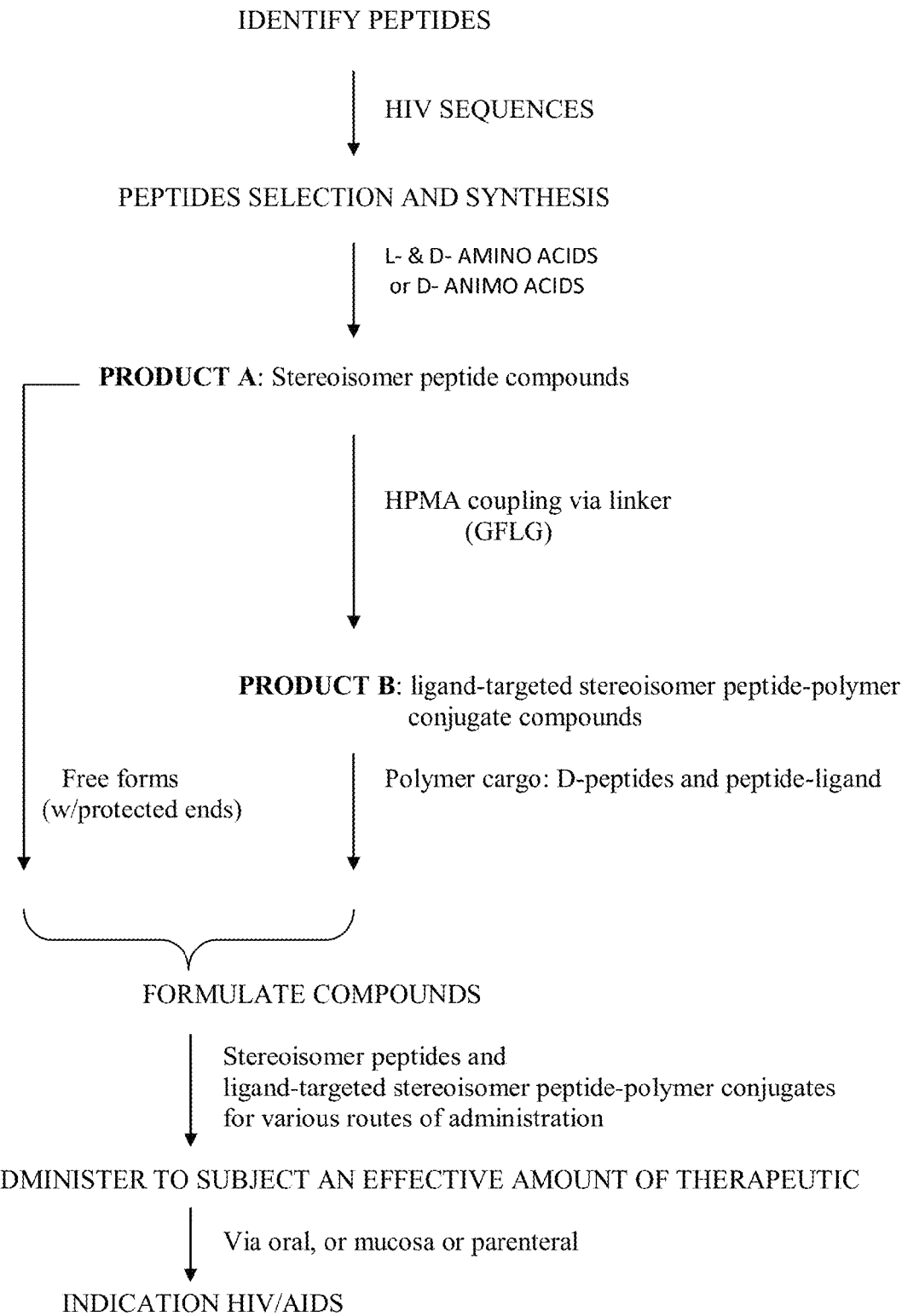
FIG. 1 shows the overall approach to create the stereoisomer peptides and their polymer conjugates, and their use in the anti-HIV strategies described in this invention.

The amino acid residues comprising the sequences of the peptides disclosed in Sequence Listing are abbreviated using a three letter code. The full names, three letter and single letter abbreviations are as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term 'peptide' refers to a polymer of amino acid residues, but preferably refers to amino acids that are alpha amino acids joined together through amide bond. Peptides are organic compounds or short polymers created from the linking of two or more α-amino acids in a defined order, and in which the amine of one is reacted with the carboxylic acid of the next to form an amide bond or a peptide bond and refer to only a few amino acid residues in length.

The term 'stereoisomer' or 'enantiomer' refers to peptides comprising amino acids that have two chiral forms that are the mirror image of each other. In this invention, the peptides comprise a mixture of D- and L-amino acids or only D-amino acids and may have two different topologies: In one topology, D-amino acids are the minor image of the naturally occurring (L-amino acid) forms, but do not have the same topology when aligned together; the second topology refers to D-peptides which have similar sequence to that of the natural L-peptides but have the positions of the carboxy- and amino-terminal residues reversed. These D-peptides are also termed retro-all-D-peptides. Most amino acids (except for glycine) are stereoisomers with L- and D-amino acids. Most naturally occurring amino acids are 'L' amino acids. The terms 'D amino acid' and 'L amino acid' are used to refer to absolute configuration of the amino acid, rather than a particular direction of rotation of plane-polarized light. The usage herein is consistent with standard usage by those of skill in the art.

The term 'amphipathic helix' refers to a protein structure that forms an alpha-helix producing a segregation of a polar and nonpolar faces with the positively charged residues residing at the polar-nonpolar interface and the negatively charged residues residing at the center of the polar face.

The term "polymer conjugate" refers to a synthetic substance consisting of chemical molecules formed from polymerization and that have conjugated a molecule such as peptide, DNA, RNA, antibody, protein, epitope, or a small chemical, fluorescent, or radioactive molecules via a linker or spacer including but not limited to oligonucleotides (di-, tri-, tetra-residues), amide, ester, peptidyl, malonate, aminomalonate, carbamate, and Schiff base.

The term "peptide ligand" refers to a peptide that binds specifically to a specific site on a viral or cellular surface protein and forms a complex. The targeting peptide ligand may be attached to the polymer using a non-degradable linker. Examples of targeting peptide ligands that provide suitable enhancing of cell targeting include but are not limited to high affinity peptides that interact with growth factors and their receptors; transport peptides that cross the blood barrier in brain, retina, and other tissues; and transduction domain, and cell penetrating peptides which cross the cell membrane.

The term "conjugate compound" refers to a composition comprising a water soluble polymer with a linker and one or two molecules bound thereto. Preferably the polymer is HPMA, the linker is a di-tri- or tetra-oligopeptide and the molecule is a stereoisomer peptide, preferably a D-peptide and a peptide-ligand with alpha-helix, or beta sheet, or cyclic structure.

The term 'carrier' refers to a water soluble polymer to which a composition, according to this invention, can be coupled. The carrier increases the molecular size of the compositions providing added selectivity and/or stability. The target molecules are delivered to tissues, cells, and sub-cellular locations. This delivery can be further enhanced by the specificity of the target molecules and a peptide-ligand conjugated to the polymer to create a ligand-targeted polymer conjugate.

The term 'formulation agent' refers to both a usually inactive substance used in association with an active substance especially for aiding in the application of the active substance, capable to reach the intended target. Inactive substances include diluents, adjuvant, excipient, or vehicle which can be sterile liquids, and vegetable or synthetic origin oils. Water or aqueous saline solutions, and aqueous dextrose and glycerol solutions, are preferably employed for injectable solutions.

As used herein, the phrase 'pharmaceutically acceptable' refers to molecular entities and compositions that are 'regarded as safe', i.e., that are physiologically tolerable and do not typically produce an allergic, toxic or adverse reaction when administered to a human. Preferably, as used herein, the term 'pharmaceutically acceptable' means being approved by a regulatory agency of the Federal or a state government or listed in the U.S. Pharmacopeia or other generally recognized pharmacopeia for use in animals, and more particularly in humans.

Identification of Peptide Sequences and Epitope Prediction

Extensive analyses of the available scientific information on HIV revealed that attempts to produce a prophylactic vaccine against HIV have failed. Vaccines against HIV have been prepared with all the HIV proteins, either individually or in mixtures usually mixed with an adjuvant or as protein fusions. Polypeptides and peptides derived from all the HIV proteins have also been used as antigens mixed with adjuvant to generate vaccines. Recombinant DNA vaccines that express the full sequence of multiple HIV proteins to prime, and MVA attenuated smallpox expressing also multiple HIV proteins to boost, have been tested. Full attenuated viral particles or whole viral membrane proteins have also been used as vaccines. In all the cases, no effective neutralizing antibodies against HIV have been raised; as a result, no vaccine against HIV has been developed.

It has been described that the reason vaccines do not work is due to the extensive sequence variability found in most of the HIV proteins making difficult to match human T-cell epitopes. The epitopes elicited by the vaccine do not match those of the infecting viral strain. It has also been indicated that high viral diversity, sequence variability, and high rates of mutation lead to an immune escape; thus, an effective AIDS vaccine must control highly diverse circulating HIV strains. This approach which considers both variable and non-variable conserved regions and that is directed to the HIV-1 Env M group, may facilitate the development of an effective T-cell based HIV-1 vaccine. The antigens are designed to express mosaics that maximize all the potential T-cell epitopes. Initial tests of this new vaccine have shown that the antigens are able to elicit certain immune response, though virus neutralization is partial.

Vaccine unsuccessful results provide the opportunity to devise alternative approaches to develop novel effective therapeutic/vaccine compounds. With this in mind, an analysis of each of the HIV protein sequences was carried out to identify novel peptides that bind a given MHC. This is important not only for rational vaccine design, but to understand why human cells fail to respond to HIV attack and invasion. The analysis of HIV sequences included the proteins Gag (matrix p17 and main core p24), Pol (protease p11, reverse transcriptase p66 and integrase p32), nucleus transport Vpr, transcription elongation factor Tat, virus release Vpu, envelope gp160 (surface gp120 and transmembrane gp41) and Vif, Rev, and Nef. The analysis was carried out by doing a sequence analysis comparison of every HIV protein against the human protein database using standard procedures such as the BLAST algorithm and searching for relevant matches between a specified query and the subject sequence. This analysis discovered that all the HIV proteins analyzed have short sequence domains covering the entire length of the protein that perfectly match about two hundred and ninety (290) human proteins. In other words, the short sequence domains of the HIV proteins have homologous sequences represented in the two hundred and ninety human proteins. This discovery is of high significance and relevance because it may explain why the anti-HIV vaccines developed so far have failed to neutralize HIV. The HIV proteins are not recognized as 'foreign' molecules by the immune system, but rather as normal components of the body. This lack of response allows the virus to 'escape' immune surveillance.

Based on this discovery, it is reasonable to assume that in order to elicit strong neutralizing antibodies against HIV by the human body, the viral antigens must have heterologous sequences to be considered 'foreign' to raise an immune response. Unfortunately, this is not the case due to the homology found between contiguous short sequences covering the entire length of each major HIV protein and short sequences of many different human proteins. This has resulted in partial or weak immune responses in individuals that have been immunized with a particular anti-HIV vaccine. Since most of the HIV antigens used to produce vaccines are made of whole viral proteins, it is reasonable to assume that these antigens are readily recognized by the immune system as part of the human body preventing the production of strong antibodies against HIV; hence the 'virus ability' to evade the immune surveillance, and, perhaps the main reason, preventing the development of an efficient vaccine. Even if we consider the high rates of HIV mutation and the sequence variability of each protein for all the HIV strains, such variability still mimics portions of sequences of many human proteins, and will therefore be considered as a 'match' or homologous sequence. Thus, trying to produce a vaccine that covers every single variation of the envelope protein of every HIV strain will not solve the problem since the HIV proteins containing the short consecutive sequence domains that have a relevant homology with a considerably number of different human proteins still match with a human protein.

The analysis using the BLAST algorithm also discovered that there are short sequences in a few HIV proteins that do not match the sequences of human proteins, but are conserved in several different strains of HIV. These short conserved sequences found only in HIV are unique because they have no homology with any human protein. These short sequences were selected and used to identify potential strong T-cell epitopes by prediction with algorithms known in the art; this resulted in the identification of 218 T-cell epitopes that strongly bind different alleles of the human Major Histocompatibility Complex (MHC), the large genomic region or gene family found in most vertebrates. These epitopes will be recognized by the immune system as 'foreign' inducing the generation of strong binding antibodies. Mixtures of these peptide epitopes in a 'cocktail' could be used to develop an anti-HIV-1 therapeutic-vaccine.

When these specific peptide antigens are synthesized and chemically modified to create the stereoisomer peptides with protected ends, they become novel stereoisomer peptide antigens that are quite different from the natural and/or recombinant peptides, polypeptides, and proteins used in traditional vaccines mixed with adjuvant like oil emulsions or protein fusions.

Protein databases and software tools to retrieve and analyze protein sequences are well known in the art and are available through the National Center for Biotechnology Information (NCBI) under Entrez Protein which is a search and retrieval system for proteins compiled from a variety of sources, including SwissProt, TrEMBL, PIR, PRF, PDB, UniProt and translations from annotated coding regions in GenBank and RefSeq. The ExPASy Proteomic Server of the Swiss Institute of Bioinformatics contains a variety of proteomic tools for protein and peptide analysis and a variety of programs for similarity searching and protein comparisons. The European Bioinformatics Institute of the European Molecular Biology Laboratory (EBI-EMBL) as well as the Protein Information Resource (PIR) at Georgetown University Medical Center and the National Biomedical Research Foundation (US) are part of this universal knowledgebase of proteins.

The NCBI server and the ExPASy proteomics server provide a variety of software tools for protein analysis. Protein sequences of interest can be retrieved from NCI Protein Entrez and analyzed with a variety of comparison algorithms and other programs available in both databases. For example, the UniProt knowledge database can be used to retrieve protein sequences; the ViralZone is a portal to viral UniProtKB/Swiss-Prot entries; and PROSITE can be used to retrieve protein families and domains.

For sequence comparison, typically one sequence acts as a reference sequence, to which test sequences are compared. Test and reference sequences are input into a computer, subsequent coordinates, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted with the BLAST algorithm. The parameters W, T, and X determine the sensitivity and speed of the alignment. For amino acid sequences, the BLASTP program uses as defaults a word length (W) of 3, an expectation (E) of 10 and the BLOSUM62 scoring matrix described in the art (Proc. Natl. Acad. Sci. USA 89:10915, 1989). In addition to calculating percent sequence identity, the BLAST algorithm also performs a statistical analysis of the similarity between two sequences according to the art (Proc. Natl. Acad. Sci. USA, 90 (12): 5873, 1993). The similarity provided by the BLAST algorithm is the smallest sum probability (P(N)), which provides an indication of the probability by which a match between two amino acid sequences would occur by chance.

The analysis of the HIV protein sequences using the BLAST algorithm, resulted in the identification of short protein domains of HIV-1 that do not overlap with human protein sequences from which the epitopes recognized by the MHC were predicted. Other homology algorithms include GAP, BESTFIT, FASTA, and TFASTA (Wisconsin Genetics Software Package) or by visual inspection. A useful algorithm is PILEUP, which creates a multiple sequence alignment from a group of related sequences using progressive, pairwise alignments to show relationship and percent sequence identity.

The identification of strong T-cell epitopes was carried out using prediction algorithms based on HLA-binding motifs and peptide specific T cells which are generally understood in the art and can be determined, for example, using the NetMHC (Vaccine 23: 5212, 2005) and SYFPEITHI (Immunogenetics, 50(3-4):213, 1999) algorithms. The NetMHC and SYFPEITHI algorithms identify peptides that bind MHC-1 (major histocompatibility complex class I) molecules. Finding peptides that bind a given MHC is important for rational vaccine design and disease diagnostics. The artificial neural network method in NetMHC (Protein Sci, 12, 1007, 2003; Tissue Antigens 63(5):395, 2004) is the best among available methods. This algorithm predicts 8-, 10- and 11-mer peptide binding using 9-mer trained predictors, which extend the MHC coverage for these peptide lengths significantly compared to other available MHC peptide-binding algorithms.

The second algorithm (SYFPEITH) is a database for MHC ligands and peptide motifs that facilitates the search for peptides and allows the prediction of T-cell epitopes ranging from 8-mer to 15-mer. The prediction is based on published motifs (pool sequencing, natural ligands) and takes into consideration the amino acids in the anchor and auxiliary anchor positions, as well as other frequent amino acids. The scoring system evaluates every amino acid within a given peptide. The allocation of values is based on the frequency of the respective amino acid in natural ligands, T-cell epitopes, or binding peptides. The reliability of SYFPEITHI epitope prediction algorithm is that only those MHC class I alleles for which a large amount of data is available are included in the "epitope prediction" section of SYFPEITHI. A reliability of at least 80% in retrieving the most apt epitope can be expected. Thus the naturally presented epitope should be among the top-scoring 2% of all peptides predicted in 80% of all predictions. Though the large number of human MHC-I molecules make the selection of appropriate prediction algorithms difficult, the algorithms used here (NetMHC and SYFPEITHI) to select epitopes seem to be the best prediction algorithms across all HLA molecules. In this invention, only epitopes predicted to be strong binders (below 50 micro molar) or with high scores (above 15), for each algorithm, respectively, were selected.

The structural properties and characteristics of all the HIV proteins in complexes with small chemical molecules, peptides or proteins, and their interactions with other molecules was also analyzed using the prediction tools, scientific literature on the 3D structure of the proteins and cell-based experiments. Such analyses discovered short sequence domains in the HIV proteins with Cys residues that form cyclic peptides with constrained structures via disulfide bonds and sequence domains with linear alpha-helix structures; all important for viral function, replication, and survival.

Since the HIV gp160 envelope glycoprotein is the major target for therapeutic drugs and vaccines, and it is the major protein involved in viral entry and fusion with the host CD4 cells, this protein including subunits, gp120, and gp41, were analyzed. Viral function, replication, and survival are crucial functions that depend on the proper folding of gp120 and gp41 to achieve the formation of the six-helix bundle structure that forms the hydrophobic pocket that brings the virus and cell membranes close together, allowing fusion of the membranes and subsequent entry of the viral core into the host cell.

Several short peptides containing Cys residues in the sequence domains of HIV gp160 were identified and selected for the ability to form cyclic structures via disulfide bonds. These peptides, with constrained structures, are expected to bind and disrupt the formation of the six-helix bundle of the HIV gp160 protein complex, and to block the HIV envelope proteins which are the viral specific docking proteins for the cellular CD4 co-receptor protein. This can be done by competing with the native structures that interact to form the gp160 complex. This membrane layer is essential for viral entry into the host cell to become part of the host and replicate. The peptides with Cys residues are therefore aimed to block the earliest step (i.e., entry) of infection rather than eliminating virus that is replicating in CD4 infected cells and hiding in latent reservoirs.

A similar analysis also identified short sequence domains of gp160 that have linear alpha-helix structure. These short peptides have a net positive charge with 3 to 10 hydrophobic residues in one side of the chain forming the alpha-helix; the peptides mimic HIV sequences and resemble the properties of antimicrobial peptides of having a net positive charge and a short, amphipathic helical structure, and it is expected that these peptides will interact and cross the viral membrane bather causing disruption of the membrane.

Designing, optimizing, and synthesizing target specific stereoisomer peptides with constrained cyclic and/or alpha-helix structures and modified ends result in functional, non-toxic, stable, protease resistant, and structurally more rigid cyclic and linear stereoisomer peptides, which constitute the compositions that are further conjugated to the preferred polymer to create the novel polymer—conjugate compounds which constitute the subject matter of this invention.

Peptides of the Invention

In one aspect, this invention discloses two hundred and ninety eight peptides (298) with sequences labeled SEQ ID NO 1 through SEQ ID NO 298, sizes ranging from 4 to 54 amino acids in length, but with the majority of the peptides between 8 to 15 amino acids in length.

One particular aspect of this invention is that all the peptides mimic short sequences in the HIV proteins, and therefore, will compete, bind or block he activity of the HIV protein and/or the interaction of other molecules with the target HIV protein. The HIV-1 proteins with domains targeted by the peptides include Gag (matrix p17 and main core p24), Pol (protease p11, reverse transcriptase p66 and integrase p32), nucleus transport Vpr, transcription elongation factor Tat, virus release Vpu, envelope gp160 (surface gp120 and transmembrane gp41), and Vif, Rev and Nef. These proteins are targeted by the peptides by the step of contacting a particular protein with a particular composition, prepared according the present invention, and that directs such activity into the cells. The compositions of the invention target the proteins by competing, blocking, inhibiting, and disrupting a folding structure, an activity, or a functional site which can be protein-protein interaction sites; substrate, receptor, or ion binding sites; phosphorylation sites; folding loop sites. Endocytosis of the composition into the cells allow entering the D-peptides inside the cell cytoplasm or nucleus affecting, binding, blocking or competing with other molecules for the target sites of the proteins. Particularly in this invention, the cells are lymphocytes and CD4 cells, among others.

In another aspect, this invention discloses 218 linear peptides from the group of 298 peptides with sequences labeled SEQ ID NO: 1 through SEQ ID NO: 218, ranging from 8 to 15 amino acids in length. These peptides, as described previously were found to be strong T-cell epitopes determined by prediction algorithms based on HLA-binding motifs and peptide specific T cells. Sixteen (16) peptides with sequences labeled SEQ: ID NO: 235 through SEQ. ID. NO: 250, with sizes ranging from 12 to 54 amino acids in length, and that mimic several short domains of all the major HIV proteins, correspond to the peptide sequences that do not overlap with human proteins upon comparison using the BLAST algorithm. These peptides sequences were used to predict the 218 peptides with strong T-cell epitopes.

In another aspect of this invention, the peptides when are synthesized and chemically modified refer to stereoisomer peptide compounds with mixtures of L- and D-amino acids or only D-amino acids in their sequences giving rise to alternative stereo-chemistries which will be readily appreciated by those skilled in the art. Peptides comprising D-amino acids are the preferred form of the peptides of this invention.

Both chiral changes and end terminal protection creates peptide compounds that are resistant to proteolysis and can readily be conveniently administered by the oral or mucosa routes. A review of the available literature shows that combinatorial libraries with multiple alternating L- and D-amino acids or synthesizing peptides containing only D-amino acids or making a protein or an enzyme entirely of D-amino acids helps to enhance their stability and resistance to degradation by enzymes. Peptide chirality (i.e., D- and L amino acids or only D-amino acids) is not necessarily required for biological activity or for peptide-peptide interactions within the membrane environment, and therefore they should exert their biological activity like their natural counterparts (L-forms) do. Furthermore, peptides with D-amino acids are not degraded by proteases providing potential for oral bioavailability, since they have extended persistence in circulation, long shelf life, and can be used in harsh mucosal environments as a topical prophylactic microbicide, and are resistant to hydrolysis. Natural and synthetic peptides with L-amino acids lack all these properties in vivo; in fact, peptidases break peptide bond in L-peptides by inserting a water molecule across the bond.

Generally, L-peptides are broken down by peptidases in the body in a manner of a few minutes or less. In addition, some peptidases are specific for certain types of L-peptides, making their degradation even more rapid. Thus, if a peptide is used as a therapeutic agent, its activity is generally reduced as the L-peptide quickly degrades in the body due to the action of peptidases; in this invention, instead of synthesizing the peptides in their naturally occurring forms (L-peptides), the chirality of the amino acid sequence is changed by synthesizing the peptides with mixtures of D- and L-amino acids or entirely with D-amino acids, the preferred form, to create stereoisomer peptide compounds with enhanced stability, solubility, and resistance to degradation by enzymes. These enhanced physicochemical properties made target specific stereoisomer peptides suitable to develop novel stable drugs for therapeutic use.

This invention also provides peptide compounds with modified ends. The peptide ends are chemically modified during synthesis by acetylating the N-terminal group and amidating the C-terminal group using standard chemistries. These additional modifications mimic a peptide bond at the end of the peptide, further increasing their stability to proteases and further yielding enhanced pharmaceutical properties. The N-terminal group is not protected when the peptide is conjugated to a linker.

In other aspect, this invention discloses a group of thirty (30) peptides from the set of 298, labeled SEQ ID NO: 219 through SEQ ID NO: 234, ranging from 7 to 45 amino acids in length, with two, four or six Cys residues that form single, double or triple intra-molecular disulfide bonds, respectively, via oxidation. Cyclic conformations obtained via disulfide bond during chemical synthesis result in D-peptides with constrained cyclic structure. The number of Cys residues in the sequence determines the number of disulfide bonds and the rigidity of the cyclic D-peptide. These peptides with constrained structures are more stable and resist degradation by proteases found in human fluids including serum, plasma, blood, saliva, urine, tears and mucosal secretions, and since sequences mimic a particular specific functional domain of the target protein, they are expected to bind, block and/or disrupt the formation of the six-helix bundle of the HIV gp160 protein complex by competing with sequences involved with the normal function of this protein in vivo.

Synthetic constrained peptides have significant reduced conformational space compared to their linear homologues. Incorporation of a second or third disulfide bond results in significant overall rigidity. Thus, it is expected that the cyclic conformation created by formation of disulfide bonds in some of the D-peptides, will enhance competition and binding of the peptide to the target HIV gp160 envelope glycoprotein, by competing with sequence domains involved in the function of this protein. Six of these peptides (SEQ ID NOs: 219, 221, 222, 223, 224, and 225) form single disulfide bond, and one peptide (SEQ ID NO: 220) form a triple disulfide bond. These peptides target protein domains of HIV-1 gp160 that are important for both viral replication and protein folding. By blocking these functions, protein folding deficiencies will disrupt virus replication. One peptide with a single disulfide bond (SEQ ID NO: 226) targets the loop joining the HR1 (N-Helix) and HR2 (C-Helix) ectodomains of HIV-1 gp41 which is essential for viral replication. In addition, peptides labeled [SEQ ID NO: 227], [SEQ ID NOs: 228, 232, and 234], and [SEQ ID NOs: 229, and 230], form single, double, and triple disulfide bonds. These peptides, with constrained structures, target the highly conserved region of HIV-1 gp41 N-trimer pocket; one additional peptide with a single disulfide bond (SEQ ID NO: 231) binds both CD4 and gp41. Additional cyclic peptides (SEQ ID NOs: 293, 295, 296, and 298) with single disulfide bond, and with double disulfide bond (SEQ ID NO: 294) target also domains of HIV gp120 protein.

In one more aspect, this invention discloses a group of peptides from the set of 298 comprising fifteen (15) peptides, labeled SEQ. ID NO: 251 through SEQ ID NO: 265, ranging from 9 to 29 amino acids in length, with linear alpha-helix structure formed by the aliphatic and aromatic hydrocarbon side chains of hydrophobic amino acids. These peptides have a net positive charge ranging from +1 to +4 with 3 to 10 hydrophobic amino acids in one side of the chain. The peptides mimic sequence domains present in HIV gp 160 and other HIV proteins and are expected to disrupt protein-protein interactions in the CD4 cell surface, and block the entry and fusion of the virus into the host cell. HIV gp 160 is the viral specific docking protein for the cellular CD4 co-receptor protein. This membrane layer is essential for viral entry into the host cell to become the host and replicate. Disrupting the viral membrane via these positively charged linear alpha-helix peptides, will prevent viral infection. These sequences resemble antimicrobial peptides including positive net charge, and hydrophobic and hydrophilic amino acid residues arranged in an amphipathic-helix; these properties, generally understood in the art, determine their structure/function relationships and their interactions with cell membranes.

Peptides with amphipathic-helix can bind bacteria not only with hydrophobic interactions but also through electrostatic interactions, and can disrupt the bacterial membrane integrity resulting in depolarization of the cell membrane as observed with natural antimicrobial peptides such as minidefensins and cathelicidin. Protein folding deficiencies, disruption of protein-protein interactions, and inhibition of viral replication has also been observed with unrelated alpha-helix peptides. These examples illustrate the negative effects that a particular linear structure and residues in a peptide may have on cells and macromolecules. The sequences of the linear peptides of this invention share similar structures to those present in antimicrobial peptides, and therefore a negative protein-protein interactions and membrane depolarization is expected by the particular peptides of this invention upon interaction with the target proteins.

In yet another particular aspect of this invention, one peptide with sequence labeled SEQ ID NO: 265 with 13 amino acids is a peptide that mimics the Tat HIV transduction domain. This peptide forms an alpha-helix and has a net charge of +4 and 46% hydrophobic residues, 5 of which are in one side of the chain forming the helix. The amino acid sequence of this peptide was modified to further strengthen the alpha-helical content, to enhance the transduction potential compared with the native Tat sequence. This peptide also resembles a bacterial peptide, and thus it is a cell penetrating peptide (CPP) that can be used in its modified form as peptide ligand attached to the polymer via a linker, preferably non-degradable, to enhance the delivery of other peptides of this invention to tissues, cells, and sub-cellular locations.

In still another aspect, this invention discloses a group of 18 peptides from the set of 298 labeled SEQ ID NO: 266 through SEQ ID NO: 283, ranging from 4 to 7 amino acids in length. Except for SEQ ID NO 274 and 275 which are cyclic peptides, the rest are linear beta-sheet peptides and all these peptides mimic conserved domains of several HIV-1 target proteins.

In other aspect, this invention also discloses a group of nine (9) peptides from the set of 298, labeled SEQ ID NO: 284 through SEQ ID NO: 292, ranging from 4 to 31 amino acids in length containing two, or six cysteine residues that form single or triple intra-molecular disulfide bonds, respectively, via oxidation to obtain cyclic structures. These peptides specifically target the HIV-1 proteins gag24, p2p7p1p6, protease, integrase, vif, and tat, respectively. Any disruption in protein folding, and protein-protein interactions by these peptides, in their synthetic stereoisomer forms with modified ends, or in their polymer conjugate forms, will affect viral replication. In the case of native HIV Tat protein, folding, and function is determined by essential disulfide bonds. Blocking this folding region with one or more of the peptides of this invention will render Tat non-functional.

In a particular aspect, this invention discloses one peptide from the set of 298, labeled SEQ ID NO: 298 with 13 amino acids that have liner alpha-helix structure with a positive net charge +4 with 53% hydrophobic amino acids in one side of the chain; this structure resembles an antimicrobial peptide, and thus is a cell penetrating peptide (CPP). This peptide mimics a domain of human lens ephithelium derived growth factor and therefore is a competitive ligand. This peptide can be used as targeted peptide ligand attached to a particular polymer carrier via a linker or spacer to enhance the delivery of other peptides of this invention to tissues, cells, and sub-cellular locations.

Synthesis of Peptides

This invention employs, except where otherwise indicated, standard techniques for the synthesis and manipulation of peptides, and features peptides referred as ligands and linkers from which peptides are bound. The peptides according to the invention can be made by standard synthesis methods, although they can also be made by recombinant DNA methods. In a preferred aspect the ligands are peptides with D-amino acids and the linkers are oligonucleotides (di-, tri- or tetra-peptides) with L- or D-amino acids.

Standard techniques for solid phase synthesis are the preferred method and well known to those of skilled in the art. They are described in the arts (The Peptides: Analysis, Synthesis, and Biology. Vol. 2: pp. 3284, 1963; Solid phase peptide synthesis (2nd Ed.) Rockford: Pierce Chemical Company. P. 91, 1984). Other synthesis methods include classical solution synthesis, microwave mediated peptide synthesis, and fragment condensation. The chemical synthesis of D-peptides follow the same standard method for L-peptides, and any truncated peptides that results from long D-peptides are removed by standard HPLC, or dialysis. D-amino acids are incorporated at one or more positions in the peptide simply by using a D-form derivatized amino acid residue in the chemical synthesis. D-amino acid residues for solid phase peptide synthesis are commercially available. When peptides comprise both L- and D-amino acids, the D-amino acids can be incorporated at any position in the peptide as desired. In particularly preferred aspects of this invention, essentially every stereoisomer peptide has D-amino acids, except for Gly which has only the L-form due to its conformational structure.

Peptide Modifications: Protecting Carboxy- and Amino-terminal Groups

Chemically synthesized peptides carry free amino and carboxy terminal groups, being electrically charged in general. In order to remove this electric charge to prevent interactions with other peptides and/or proteins, especially in vivo, peptide ends are modified by N-terminal acetylation and/or C-terminal amidation. One can also modify the amino and/or carboxy terminal of the peptide compounds of the invention to produce other compounds of the invention. The amino terminal may be acetylated with acetic acid or halogenated to obtain a derivative thereof. The carboxy terminal may be amidated with carboxyamidase or amidase. Those of skill in the art recognize that a variety of techniques are available for constructing compounds with the same or similar biological activity but with more favorable characteristics in regard to their solubility, stability, and susceptibility to hydrolysis and proteolysis. The protection of the amino and/or carboxyl terminal of the subject peptide compounds of this invention, greatly improves oral delivery, and significantly increases serum half-life. A wide number of protecting groups are suitable for this purpose including but not limited to acetyl, amide, and alkyl groups. The acetyl and alkyl groups are particularly preferred for N-terminal protection and the amide groups are particularly preferred for carboxyl terminal protection. Particularly preferred carboxyl protecting groups include amides, esters, and ether-forming protecting groups. In one aspect, an acetyl group is used to protect the amino terminus and an amide group is used to protect the carboxyl terminus Preferably, acetylation is accomplished during the synthesis when the peptide is on the resin using acetic anhydride. These blocking groups also enhance the alpha-helix-forming of the peptides that have this particular structure. In this invention, preferably the D-peptides are synthesized with protected ends when they are used in their free forms. D-peptides that are conjugated to a polymer via a linker, however, have their amino group unprotected to allow for coupling the amino group of the D-peptide to the activated ONp group of a linker attached to a polymer. Protecting/blocking groups are well known to those of skill as are methods of coupling such groups to the appropriate amino acid residue(s) (Greene's Protective Groups in Organic Synthesis, 4th ed., John Wiley & Sons, Inc., 2007) herein incorporated by reference in its entirety.

Cyclization of D-peptides: Formation of Disulfide Bonds

Disulfide bridges are an important subject matter of this invention. The peptide compounds of the present invention contain one, two, or three intramolecular disulfide bonds. Such disulfide bonds are formed by oxidation of the cysteine residues by pairing the desired cysteine residues present in the sequence of a particular synthetic D-peptide. In one aspect, the control of cysteine bond formation is exercised by choosing an oxidizing agent of the type and concentration effective to optimize formation of the desired disulfide bond. For example, oxidation of the cysteine residues of a D-peptide to form one, two, or three intramolecular disulfide bonds (depending on the number of cysteine residues in the sequence of the D-peptide) is achieved using the oxidizing agent DMSO or iodine (I2). In other aspects, and preferably, the formation of cysteine bonds is controlled by the selective use of thiol-protecting groups during peptide synthesis. Where two intramolecular disulfide bonds is desired, the peptide chain is synthesized with the four cysteine residues of the core sequence protected with a thiol protecting group such as trityl(Trt), allyloxycarbonyl (Alloc), or 1-(4,4-dimethyl-2,6-dioxocyclohex-1-ylidene)ethyl (Dde). Thereafter, the thiol protecting groups are removed from the cysteine residues where the disulfide bond is desired effecting bisulfide cyclization of the monomer chain. In addition to the foregoing cyclization strategies preferred here, other non-disulfide peptide cyclization strategies such as amide-cyclization and the formation of thio-ether bonds can be employed. Thus, the compounds of the present invention can be cyclized with either an intramolecular amide bond or thio-ether bond. For example, a peptide may be synthesized wherein one cysteine of the core sequence is replaced with lysine and the second cysteine is replaced with glutamic acid. Thereafter a cyclic monomer may be formed through an amide bond between the side chains of these two residues. Alternatively, a peptide may be synthesized wherein one cysteine of the core sequence is replaced with lysine (or serine). A cyclic monomer may then be formed through a thio-ether linkage between the side chains of the lysine (or serine) residue and the second cysteine residue of the core sequence. As such, in addition to disulfide cyclization strategies, amide-cyclization strategies and thio-ether cyclization strategies can both be readily used to cyclize the compounds of the present invention.

Cyclization of D-peptides containing 2, 4 or 6 cysteine residues in L- or D-form may also be carried out through disulfide bonds using either ferricyanide assisted cyclization or glutathione assisted oxidation reaction methods well known in the art like those described in the art (Antioxid Redox Signal. 10(1):141, 2008). For ferricyanide cyclization, potassium ferricyanide is added to a solution of purified linear peptide. For a glutathione assisted oxidation, oxidized L-glutathione is added to the purified peptide. Peptides are dissolved (1 mg/mL) in 0.1% TFA and reactions take place at RT in 0.1 M NH4Ac buffer pH 7.6 stirring overnight. The progress of the reaction is judged using analytical HPLC and Mass Spectrometry analysis. The final product that is acidified (pH 4 with TFA) is isolated by preparative HPLC using an acetonitrile/water gradient in 0.1% TFA can be applied to obtain products that are greater than 95% homogeneous. The final purified products are characterized by mass spectrometry (ESI-MS or MALDI-TOF). For peptides containing two disulfide bonds a combination of trityl (Trt) and acetamidomethyl (Acm) protection groups can be chosen to selectively protect the cysteine residues so that the disulfide bond formation is predetermined The two cysteine residues at the N and C termini are protected with Trt and the two inner cysteine residues with Acm. Similar protection can be done with peptides containing three disulfide bonds. The first disulfide bond can be formed by air oxidation after selective removal of Trt and purified as described above. The second disulfide bond is generated in a single step by treatment of the Acm-protected peptide with iodine, using aqueous acetic acid as solvent to limit iodination of Tyr and Cys.

Addition of Linkers

In some aspects of the present invention, the compounds or compositions are constructed by chemically coupling a synthetic D-peptide, by covalent bond, to the water soluble polymer, preferably by way of a linker. In particular aspects, the linker, which forms a bond between the D-peptide and the water soluble polymer, refers to an enzyme-susceptible linker comprising 2, or 4 amino acids containing a cleavable site that is digested by the enzyme protease located inside cell organelles called lysosomes, which are found in the cytoplasm of most cells, and especially in leukocytes, liver, and kidney cells. Compositions according to the present invention preferably include a linker with a cleavable site by a protease, preferably situated such that the composition is within the cell, such as in a lysosome; the D-peptide can be cleaved from the linker by enzymatic digestion of the enzyme-sensitive site.

In one particular aspect the protease-susceptible linker is designed to be degraded by proteolysis in the lysosome of the target cell. The composition that is internalized by endocytosis enters an endocytic vesicle, which is transported to a lysosome. Once in the lysosome, the protease-susceptible linker is cleaved, and the D-peptide is released and transported in the cytosol. In a particular aspect of this invention, the composition may have more than two different D-peptides bound each to a separate linker conjugated to a separate branch of the preferred polymer.

In a preferred aspect of this invention, the linker or spacer is an oligopeptide with two, or four amino acid residues selected from Lys (K), Gly (G), Phe (F), Leu (L) depending on whether a specific cleavage by enzymes is required to release the drug, or the linker may be non-cleavable. Cleavable linkers include the sequences G-G-F-K, F-K, and G-F-L-G. Non-cleavable linkers have the sequence G-G. Linkers can serve as initiation site enabling binding of molecules such as peptides, oligonucleotides, small chemical molecules, antibodies, fluorescent tags, and radioactive compounds. The linker, preferably conjugated to a chemical functional group of a separate branch of a polymer by covalent bond, determines the cellular transport, clearance, cleavage, or release of the linked D-peptide. The conjugation of linkers to the polymer to create an activated co-monomer is achieved by synthesis methods well established in the art.

Peptide Ligands

Drug compounds conjugated to the polymer are to be delivered and released into the desired cell location. While linkers allow release of the drug by cleavage with enzymes, 'targeted peptide ligands' recognizing a specific binding domain of a protein, (e.g., receptor or functional sites), are also desirable. In this invention, most of the peptides comprise specific competitive anatagonists, ligands or blockers, as well as polypeptides involved in cell transduction, penetrating and transporting. These peptide ligands provide suitable enhancing of cell targeting. SEQ ID NO: 265, for example, is a modified transduction domain peptide derived from HIV Tat protein and is a cell penetrating peptide, which mediates uptake of drugs into cells. SEQ ID NO: 291 is a modified peptide derived from HIV Tat that contains the RGD sequence which interacts with integrins, VEGFR2 and other proteins in humans. The RGD sequence is flanked by two Cys residues that are added during synthesis, to create a constrained structure that enhances cell targeting and specific binding to the those proteins. SEQ ID NO: 298 is also a cell penetrating peptide with alpha-helix structure and it is derived from human LEDGF. It competes with HIV integrase binding to LEDGF protein and thus is a competitive ligand. These peptide ligands can be bound to the carrier polymer directly or with a non-degradable linker, enhancing the delivery of the peptides disclosed in this invention to tissues, cells, and sub-cellular locations.

Polymer for Peptide Delivery: N-(2-Hydroxypropyl) Methacrylamide

The selective delivery of therapeutic agents by polymers to disease tissue or cells in vivo remains a major challenge. This specification provides for the first time novel anti-HIV therapeutic compounds utilizing target specific stereoisomer peptides conjugated to a polymer, however any disease state amenable to treatment with therapeutic drugs comprising drugs conjugated to polymers could be addressed in the same way providing that the drugs are improved, or novel.

Water soluble polymers such as or HPMA have been used with small chemical molecules to create drug-polymer conjugates. The polymer selectivity is due to the manner polymer-containing compositions enter cells, which is through receptor mediated endocytosis. The polymer body distribution deliver drugs passively due to the enhanced permeability and retention (EPR) effect. Methods to synthesize HPMA to produce HPMA copolymers, the characterization of their properties and the preparation of conjugates are standard and well established in the arts (Europ. Polym. J. 9, 7, 1973; Europ. Polym. J. 10 405, 1974), and HPMA copolymers are used to carry a variety of molecules, mainly toxic cancer drugs with fluorescent or radiolabeled tags.

Attachment of polymers to bio-molecules is thought to enhance biological activity, prolong blood circulation time, reduce immunogenicity, increase aqueous solubility, and enhance resistance to protease digestion. HPMA (N-(2-Hydroxypropyl) methacrylamide) is a hydrophilic biocompatible polymer, and the HPMA copolymers are of great value as platform for delivery of drugs. HPMA can be used to conjugate macromolecules and used as a drug carrier in numerous applications and to extend the molecules half life in vivo, by enhancing the activity of drugs, and/or reducing significantly their toxicity in vivo.

HPMA is the preferred polymer of this invention to conjugate stereoisomer peptides. Conjugation of any of the peptides disclosed in this invention to HPMA in their synthetic modified form will result in novel HPMA polymer conjugates carrying target specific stereoisomer peptides. Furthermore, conjugation of two or more peptides to the polymer allows the creation of novel multi-targeted stereoisomer peptide-polymer conjugate compounds. Since the peptides have sequences that target specific domains of HIV proteins, the novel compounds created here are quite suitable for the anti-HIV-1 strategies disclosed here.

Synthesis methods to produce HPMA copolymers, characterization of properties and preparation of conjugates are well established in the art and can be employed to create polymer conjugates. In general, poly HPMA with terminal NH2 groups is synthesized by polymerization using 2,2'-azobisisobutyronitrile as the initiator in the presence of DMSO and gas argon. HPMA copolymer is purified to obtain a polymer of the desired molecular weight. This polymer with functional NH2 groups is then used to conjugate the target molecules via a linker.

Synthesis of N-(2-Hydroxypropyl) Methacrylamide

This invention employs standard techniques for the synthesis and manipulation of polymer copolymers and monomers with appropriate modifications specific to the compounds of this invention. As used herein, the term HPMA refers to N-2-hydroxypropyl methacrylamide, a hydrophilic (water soluble) polymer represented in general as HPMA homopolymer. Synthesis of HPMA, the basic unit of the polymer, is carried out in a solution of 1-amino-2-propanol (65.6 ml 0.84 mol) in 250 ml of acetonitrile, in which freshly distilled methacryloyl chloride (MACL) (41 ml, 0.42 mol) in 20 ml acetonitrile is added dropwise under vigorous stirring and cooling to −5° C. A small amount of inhibitor, tertiary octyl pyrocatechine is added to control polymerization. The reaction mixture is stirred for additional 30 min at room temperature. 1-amino-2-propanl hydrochloride formed as a byproduct is precipitated and filtered off. The filtrate is cooled at −70° C. in a dry-ice acetone bath to precipitate HPMA. After equilibrating to room temperature the product is filtered off and washed with pre-cooled acetonitrile. The pure product is isolated by re-crystallization from acetone.

Synthesis of Co-Monomers Containing GFLG Spacer/Linker

Briefly, synthesis of MA-GFLG-ONp is carried out in two steps. First MA-Gly-Phe-OH and Leu-Gly-OMe.HCl are synthesized separately. Subsequently the two dipeptides are coupled to yield MA-GFLG-OMe. The methyl group is removed with base (NAOH) yielding MA-GFLG-OH, and to this compound the reactive group p-nitrophenol is attached by esterification.

MA-Gly-Phe-OH is synthesized by dissolving 5.0 g, 22.5 mmol Gly-Phe in 5.6 ml NaOH, 4N (22.5 mmol) and cooled to 0° C. Freshly distilled Methacryloyl Chloride (MACL) (3.5 g, 34 mmol) in 10 ml of dichroromethane is added dropwise. A small amount of inhibitor (1-octyl pyrocatechine) is added to prevent polymerization of the monomers into high molecular weight oligomers. After a slight delay 8.4 ml (34 mmol) of 4N NaOH is added dropwise to the mixture. After addition of MACl and NAOH, the reaction mixture is brought to room temperature and allowed to react for 1 hour and the pH is maintained between 6 and 7. The dichloromethane layer is separated from the water layer, washed with 2 ml of water, and discarded. The aqueous layer together with the washings was mixed with 40 ml of EtOAc. HCl is then added slowly under vigorous stirring and cooling until pH 2-3 is reached. The organic layer is separated and the aqueous layer is extracted three times (3×20 ml), and then dried overnight over anhydrous sodium sulfate. The dried solution is filtered and washed with EtOAc. The EtOAc was, removed by rotary-evaporation to obtain a white powder product, which is then re-crystallized from EtOAc. Synthesis of MA-Gly-Gly-OH is carried out with the same method except that Gly is used instead of Phe residue.

Leu-Gly-OMe.HCl is synthesized by dissolving Leu-Gly (4 g. 21 mmol) in 35 ml of methanol and cooled at −5° C., followed by dropwise addition of 2 ml of SOCl2(26 mmol) under stirring. After equilibration at RT the mixture is refluxed for three hours. The solvent is evaporated to dryness and the residue dissolved in methanol and evaporated to remove HCL and SOCl2. The residues is dissolved in benzene and evaporated to obtain a while amorphous solid and used in subsequent synthesis steps.

Synthesis of Monomer MA-GFLG-OMe

Synthesis of MA-GFLG-OMe is carried out by coupling MA-Gly-Phe and Leu-Gly-OMe.HCl in 80 ml of Me-OH and cooled to 0° C.; excess of 1N NaOH is added (18 nmol) dropwise under stirring. After addition of small amount of inhibitor (1-octyl pyrocatechine) the reaction mixture is stirred for 1½ hr at 0° C., and then for 2 hours at room temperature. Methanol is removed by concentration under vacuum. 160 ml distilled water is added and the mixture is acidified to pH 2. The free acid is extracted in EtOAc (4×200 ml), washed with saturated brine and dried over anhydrous sodium sulfate overnight. Solvent is evaporated under vacuum and the tetrapeptide product is re-crystallized from EtOAc. Synthesis of MA-GG-OMe is carried out with the same method except that GG oligopeptide is used instead of the GF and LG oligopeptides.

Synthesis of Monomer MA-GFLG-OH

Synthesis of MA-GFLG-OH is carried out by adding MA-GFLG-OMe (6.9 g, 14.5 mmol) to 80 ml methanol and cooled to 0° C.; excess 1N NAOH (18 ml, 18 mmol) is added dropwise under stirring. A small amount of inhibitor, tertiary-octyl pyrocatechine is added to prevent polymerization, and the reaction is stirred for 1½ hours and then two hours at RT. The reaction mixture is concentrated under vacuum to evaporate methanol; 160 ml water are added and the mixture is acidified with concentrated citric acid to pH 2.0. The free acid is extracted with EtOAc (4×200 ml), washed with a salt saturated solution, and dried over anhydrous sodium sulfate overnight. After evaporation of the solvent under vacuum the product is re-crystallized from EtOAc. Synthesis of MA-GG-OH is carried out with the same methods except that MA-GG-OMe is used.

Synthesis of Preactivated Monomer MA-GFLG-ONp

Synthesis of MA-GFLG-ONp is carried out by adding to a solution of MA-GFLG-OH (4.7 g, 10 mmol) in 80 ml of DMF, a solution of 1.67 g of p-nitrophenol (12 mmol) in 20 ml of DMF under stirring and cooling to −10° C., followed by a solution of 2.5 g of DCC (12 mmol) in 8 ml of DMF. The reaction mixture is stirred for six hours at −10° C., and then overnight at 4° C. The precipitated byproduct DCU is filtered off and the DMF removed by rotary evaporation. The residue is dissolved in EtOAc and the remaining byproduct is filtered off. EtOAc is evaporated to dryness. The final product is soaked in ether to remove excess p-nitrophenol. This procedure is repeated several times and the purity of MA-GFLG-ONp is checked by calculating the extinction coefficient in DMSO. MA-GFLG-ONp content is assessed by release of p-nitrophenol (ONp) from the polymer in 1.0 N NaOH by UV spectrophotometry (400 nm). Synthesis of MA-GG-ONp is carried out with the same method except that MA-GG-OH is used.

Synthesis of Polymer Precursors HPMA-MA-GFLG-ONp and HPMA-MA-GG-ONp

Synthesis of polymer precursor HPMA-MA-GFLG-ONp and HPMA-MA-GG-ONp is carried out separately by radical polymerization of the corresponding monomers HPMA and MA-GFLG-ONp, and HPMA and MA-GG-ONp, respectively. These copolymers are analyzed by size-exclusion chromatography. The content of ONp groups is determined by UV/vis spectrophotometry. Briefly, polymerization is carried out using a mixture of HPMA, MA-GFLG-ONp and MA-GG-ONp at various molar ratios using the initiator 2,2'-azobisisobutironitrile (AIBN). The solution containing the monomers in desired molar ratios dissolved in acetone and mixed with the initiator is transferred to an ampoule and bubbled with nitrogen for 5 min, sealed and placed in an oil bath at 50° C. for 24 hours under stirring. After 24 hours the copolymers would precipitate out of solution and the ampoules are cooled to room temperature and placed in the freezer for 20 minutes to increase the yield of the precipitated polymer further. The copolymers are filtered off, dissolved in methanol, and precipitated in ether. After filtration and washing with ether the copolymers are dried under vacuum. The polymer conjugates can be analyzed by size exclusion chromatography. These two polymer precursors can also be obtained as pre-activated para-nitrophenol ester directly from the supplier.

Synthesis of Polymer Conjugates Containing Ligand-Targeted HPMA-GG-PL, and Conjugates Containing Stereoisomer-Peptides HPMA-GFLG-D-Peptide Synthesis of polymer conjugates is carried out using the precursor HPMA-MA-GFLG-ONp to couple a D-peptide (target specific and epitopes) to the polymer backbone via degradable "GFKG" linkers to generate a HPMA-GFLG-D-Peptide polymer conjugate, or using the precursor HPMA-MA-GG-ONp to couple a 'peptide-ligand' (PL) (transduction domain or cell penetrating peptides) to the polymer backbone via non-degradable "GG" linkers to generate a HPMA-GG-PL polymer conjugate. Briefly, the precursor HPMA-MA-GFLG-ONp (20 mmol ONp) and D-peptide (26 mmol) are dissolved in 400 μl DMF. 30 ml of N,N-diisopropylethylamine (DIPEA) (177 mmol) diluted in DMF (1:1, v:v) is added slowly dropwise with a Hamilton micro-syringe while stirring the mixture at room temperature in the dark overnight. Unreacted ONp groups are deactivated (hydrolyzed) with 1-amino-2-propanol (2 ml), the mixture containing HPMA-GFLG-D-peptide is diluted into deionized water. The solution is dialyzed intensively and then lyophilized. A conjugate with high PL content is synthesized similarly using polymer precursor HPMA-MA-GG-ONp. The exact PL or D-peptide content of each separate conjugate is determined by amino acid analysis.

Synthesis of Monomers MA-GFLG-D-peptide and MA-GG-PL with Conjugated Peptides

Alternatively, MA-GFLG-D-peptide and MA-GG-PL monomers can be synthesized each separately following the procedure described above except that the monomer precursor MA-GFLG-ONp is used to attach D-peptide and MA-GG-ONp is used to attach PL. Briefly, the monomers MA-GFLG-ONp (20 mmol ONp) and D-peptide (26 mmol), and MA-GG-ONp (20 mmol ONp) and PL (26 mmol), are dissolved in 400 μl DMF is separate reactions; 30 ml of N,N-diisopropylethylamine (DIPEA) (177 mmol) diluted in DMF (1:1, v:v) is added to each mixture slowly dropwise with a Hamilton micro-syringe while stirring the mixture at room temperature in the dark overnight. Unreacted ONp groups are deactivated (hydrolyzed) with 1-amino-2-propanol (2 ml), the mixture containing MA-GFLG-D-peptide or MA-GG-PL is diluted with deionized water. The solution is dialyzed intensively and then lyophilized. The exact PL or D-peptide content of each separate monomer is determined by amino acid analysis.

The monomers MA-GFLG-D-peptide and MA-GG-PL are then polymerized with HPMA via radical polymerization of the monomers using AIBN (2,2'-azobisisobutyronitrile) as the initiator in the presence of DMSO and the inert gas argon to obtain the polymer conjugate HPMA-GFLG-D-peptide-GG-LP which contains one D-peptide coupled via a degradable GFLG linker and a peptide-ligand conjugated via a non-degradable GG linker. The peptide-ligand (PL) can be an epitope, or a transduction peptide, or a receptor binding peptide, or a cell penetrating peptide to guide the polymer to tissue, cells, or sub-cellular locations and deliver the D-peptide to the target protein to compete, bind, or block a functional site.

Synthesis of Monomer MA-PL without Linker

Alternatively MA-PL (peptide-ligand) can be synthesized directly without a GG linker by mixing 0.1 mmol of the peptide-ligand in 1 ml of 0.1N NaOH (0.1 mmol) and cooled at 0° C. Freshly distilled MACl (15.6 mg, 0.15 mM) in 1 ml of dichloromethane is added drop wise a room temperature and allowed to react for one hour while maintaining the pH around 6-7. The organic layer is separated from the water layer, washed with 2 ml of water, and discarded. The aqueous layer together with the washings is mixed with 40 ml of EtOAc. Under vigorous stiffing and cooling, HCl is added slowly until pH reaches 2-3. The organic layer is separated and the aqueous layer is extracted 3× with EtOAc (3×20 ml). The extracted layers are dried over anhydrous sodium sulfate overnight. The dried solution is filtered and washed with EtOAc, which is later removed with a rotary-evaporator to obtain the final product as a white powder, which is re-crystallized from EtOAc.

Copolymerization of Monomers HPMA, MA-PL and Preactivated Monomer MA-GFLG-ONp

The polymerization is carried out using mixtures of HPMA, MA-PL and MA-GFLG-ONp at various molar ratios using the initiator 2,2'-azobisisobutironitrile (AIBN). The solution containing the monomers in desired molar ratios dissolved in acetone and mixed with the initiator is transferred to an ampoule and bubbled with nitrogen for 5 min, sealed and placed in an oil bath at 50° C. for 24 hours under stiffing. After 24 hours the copolymers precipitate out of solution and the ampoules are cooled to room temperature and placed in the freezer for 20 minutes to increase the yield of the precipitated polymer further. The copolymer is filtered off, dissolved in methanol, and precipitated in ether. After filtration and washing with ether the copolymer is dried under vacuum. The molecular weight of the ligand-targeted copolymer HPMA-GFLG-ONp-PL, is analyzed by HPLC.

Coupling D-Peptides to Ligand-Targeted Pre-Activated Copolymer HPMA-GFLG-ONp-PL

The copolymer precursor HPMA-MA-PL-MA-GFLG-ONp (20 mmol ONp) and D-peptide (26 mmol) are dissolved in 400 µl DMF. 30 ml of N,N-diisopropylethylamine (DIPEA) (177 mmol) diluted in DMF (1:1, v:v) is added slowly dropwise with a Hamilton micro-syringe while stirring the mixture at room temperature in the dark overnight. The reactive ester groups (i.e., carboxyl groups of residues converted to p-nitrophenyl ester) of the pre-activated copolymer HPMA-PL-GFLG-ONp are reacted with the D-peptide via nucleophilic attack of the amino groups (alpha-amino) forming amide linkages with the linker. D-peptides can also be bound to the linker by the ε-amino group of L-Lys residue attached to the linker or to the ε-amino group of a D-Lys residue in the D-peptide. Unreacted ONp groups are deactivated (hydrolyzed) with 1-amino-2-propanol (2 ml), the mixture containing the final product HPMA-PL-GFLG-D-peptide is diluted in deionized water. The solution is dialyzed intensively and then lyophilized The exact content of PL and D-peptide is determined by amino acid analysis.

The pre-activated copolymer HPMA-GFLG-ONp is also commercially available; this allows the eliminations of several synthesis steps to facilitate the rapid preparation of the novel compounds. This can be carried out by coupling the amine group of different D-peptides directly to HPMA-GFLG-ONp in separate reactions, and then copolymerize them all together with the monomer MA-GG-PL to prepare a ligand-targeted multi-D-peptide-polymer conjugate of the form HPMA-[GFLG-D-peptide]x3-GG-PL. In general, these copolymer conjugates are synthesized via p-nitrophenyl ester aminolysis of the pre-activated copolymer precursor forming amide linkages between the reactive p-nitrophenyl ester groups of the linker and the amino groups, preferably ε-amino groups, in the D-peptide. This reaction is carried out by adding a solution of the D-peptide in DMF (dimethyl-formamide) and triethylamine (5:1), and the mixture is stirred overnight, at room temperature while protected from direct light, after which it is diluted with water (3 ml), dialyzed extensively against distilled deionized water and then lyophilized and stored at −20° C.

The skilled artisan will recognize that variations of the synthesis described in this specification may be used without departing from the spirit and scope of the invention. For example the D-peptide (1.3 times excess molar equivalents) may be dissolved in dry N,N-DMF under constant stirring followed by addition of dry pyridine (1:1 molar equivalents relative to the polymeric ONp content) and polymeric precursor in dry DMF. The reaction mixture is bubbled with nitrogen and continuously stirred at room temperature for 22 hours at 50° C. The reaction is terminated with 1-amino-2-propanol. The crude conjugate is dialyzed against deionized water, lyophilized, and stored at −20° C. The peptide content in the conjugate is determined by amino acid analysis. The conjugate molecular weight is estimated by size exclusion chromatography.

The molecular weight of the branched polymer precursor and the polymer conjugate is approximately 30 to 50 KDa with about 30 KDa for the precursor and about 45 KDa for the conjugate. The term "about" indicates that in preparations of hydrophilic HPMA, some molecules will weigh more, some less, than the stated molecular weight. The final molecular weight will depend on the polymerization reaction that determines the number of branches desired in the polymer, the size of the peptide-ligand, and the target specific D-peptide conjugated to HPMA copolymer pre-activated precursor, which can be determined by gel-filtration chromatography, and the peptide content in the conjugate can be determined by amino acid analysis.

The synthesis of ligand-targeted polymer conjugates carrying each a single D-peptide and the targeted peptide-ligand (PL) (with or without a linker) are referred in this invention as stereoisomer peptide-polymer conjugate compounds and constitute a subject matter of this invention. These conjugate compounds can be evaluated using in vitro and in vivo assays to determine the ability of the specific D-peptide to compete, bind, block, or inhibit a functional group of the corresponding target protein.

The synthesis of ligand-targeted polymer conjugates carrying each more than one different D-peptide and the targeted peptide-ligand (PL) (with or without a linker) are referred in this invention as multi-stereoisomer peptide-polymer conjugate compounds and constitute the subject matter of this invention. These multi-peptide polymer conjugates can be synthesized by mixing more than one D-peptides and the peptide-ligand (PL) in the reaction mixture to generate polymer conjugates containing randomly distributed D-peptides with different sequences and PL. However, this approach may provide heterogeneous amounts of the different D-peptides; therefore to generate multi-d-peptide polymer conjugates with homogeneous amount of each peptide, the monomers carrying the D-peptides and PL are preferably synthesized separately, and then polymerized to create the targeted polymers with different D-peptides and PL.

It is also desirable to synthesize separately, for example, three different polymer conjugates; two carrying each a different D-peptide and one carrying PL. These individual conjugates are purified and then mixed in equivalent molar ratios. These mixtures of polymer conjugates carrying different D-peptides and PL are also referred in this invention as multi-stereoisomer peptide-polymer conjugate compounds since the mixture comprises different D-peptides and constitute the subject matter of this invention. Evaluation of the mixture ('cocktail' approach) of polymer conjugates can be done using in vitro and in vivo assays to determine the ability of the D-peptides in the mixture of conjugates to compete, bind, block, or inhibit a domain that corresponds to a functional site of the target HIV protein. The synthesis of both polymer conjugates with single D-peptide and with multiple D-peptides is further illustrated in examples 2 and 3.

Use of Stereoisomer Peptides and Their Conjugates

The stereoisomer peptide compounds, the stereoisomer peptide-polymer conjugate compounds, and the multi-stereoisomer polymer-peptide conjugate compounds of this invention, are useful in assays in vitro to determine their inhibitory activities (IC50) in different strains of HIV-1 and to determine the polymer's transport properties, efficiency of internalization, permeability, retention and biodistribution in vivo in PBMC cells, leukocytes, CD4+ cells or other mammalian cell sources, as well as their binding or internalization in different viral particles including the cleavage and release of the D-peptides into the cytosol. Polymer HPMA is an effective delivery system of 'cargo' molecules (D-peptides) based on its well known cellular uptake, and efficient internalization into cells by the endocytic pathway. The compounds, with sequences that mimic the corresponding domain of a target HIV protein, can also be used as reagents for determining the biodistribution of the stereoisomer peptides and their conjugates in human cells in vitro, and their potential activity to inhibit different HIV-1 strains that have been inoculated and infected a variety of mammalian cells. By labeling such peptides, one can identify cells having conjugates on their surfaces or in subcellular locations. This can be achieved by radiolabeling the conjugates with 99mTc or 90Y or using fluorescent molecules (e.g., FITC). In addition, based on their ability to bind or enter a human cell, the stereoisomer peptides and their conjugates of the present invention could be used in Western blotting, ELISA, FACS analysis, to name a few. In addition, the compounds of the present invention may be used in purifying cells expressing HIV-1 proteins on the cell surface or inside the cells based on their predicted ability, for example, to interact and bind specific HIV-1 proteins and CD4+ cells.

The compounds can also be utilized as commercial reagents for various research and diagnostic purposes including but not limited to: antigen-antibody binding and complexes formation using commercially available HIV-1 antibodies; antagonist or blocking reagents in random peptide screening aimed at finding antigens in uncommon HIV-1 strains or co-infections with different HIV-1 strains, or to raise antibodies specific to a particular HIV protein.

In another aspect of the present invention, methods of treatment are provided. The stereoisomer peptide compounds and their conjugate compounds of this invention may be administered to a mammal, i.e., mice, monkeys, humans, to prevent HIV-1 infection or to treat HIV-1 infection, or to treat disorders associated with HIV-1 infection such as the acquired immune deficiency syndrome (AIDS). The methods comprise administering to a subject formulated stereoisomer peptide compounds or stereoisomer peptide-polymer conjugate compounds, or multi-stereoisomer peptide-polymer conjugate compounds to prevent HIV-1 infection or to kill the virus replicating in infected cells, and thus, helping alleviate the symptoms associated with AIDS, which constitute a subject matter of this invention.

Pharmaceutical Compositions

Pharmaceutical compositions of the stereoisomer peptides and their polymer conjugates can be administered to alleviate or modulate a condition. Such pharmaceutical compositions may be for administration by oral, transmucosal (nasal, vaginal, rectal, or sublingual), parenteral (intramuscular, intraperitoneal, intravenous (IV) or subcutaneous injection), transdermal (passively), and pulmonary routes of administration, and can be formulated in dosage forms appropriate for each route of administration. In general, comprehended by the invention the pharmaceutical compositions comprise effective amounts of the compounds, i.e., stereoisomer peptides in free form or single and/or multi stereoisomer peptide polymer conjugate compounds, together with pharmaceutically acceptable diluents, solubilizers, emulsifiers, anti-oxidants, preservatives, bulking substances, adjuvants and/or excipients. The compositions of the present invention may be formulated for administration by several routes according to a variety of methods known to one of ordinary skill in the art, including for example, but not limited to methods describe in Martin E W (1990) Remington's Pharmaceutical Sciences. 8th Ed. Mack Publishing Co., Easton, Pa. 18042) pages 1435-1712; Marshall K (1979) In: Modem Pharmaceutics Edited by G. S. Banker and C. T. Rhodes Chapter 10, 197; U.S. Pat. Rhodes Chapter 10, 197; U.S. Pat. No. 5,391,377; Abuchowski and Davis (1981) in Enzymes as Drugs. Hocenberg and Roberts, eds. (Wiley-Interscience: New York, N.Y.) pp. 367-383, and U.S. Pat. Nos. 6,706,289 and 5,320,840 to formulate pharmacological agents conjugated to polymers, hereby incorporated by reference.

Oral Delivery

Unlike typical peptide formulations with L-peptides, the peptides of this invention comprise stereoisomer peptides in free form or stereoisomer peptide polymer conjugate compounds with the same D-peptide or 2 or more D-peptides, which can be administered orally, without protection against proteolysis by stomach acid. Furthermore, since they are conjugated to a functional group of HPMA polymer carrier, the oral bioavailability of the compounds is enhanced, but can be further be enhanced by using protective excipients. For formulation purposes, this is typically accomplished either by complexing the compound with a composition to render it resistant to acidic and enzymatic hydrolysis or by packaging the compound in an appropriately resistant carrier in solid forms. In general, the formulation includes the stereoisomer peptides in free form or in the form of polymer conjugates using inert ingredients which allow for release of the biologically active material in the intestine. Also contemplated for use herein are liquid dosage forms for oral administration, including pharmaceutically acceptable emulsions, solutions, suspensions, and syrups, which may contain other components including inert diluents, adjuvant, emulsifying and suspending agents; and sweetening and flavoring agents.

In preferred aspects, the peptide compounds are chemically modified to enhance their pharmaceutical properties so that oral delivery is efficacious. These enhanced properties are also ideal for administration in harsh environments via the mucosa. In particular, the compounds of this invention can be orally administered to a mammal, and are readily taken up by the cells lining the intestine and delivered to the serum via the endocytic pathway. The modifications facilitate their uptake into the blood stream from the digestive/intestine system.

For oral formulations, the location of release may be the stomach, the small intestine, or the large intestine. Preferably, the release will avoid the deleterious effects of the stomach environment, either by protection of the stereoisomer peptide or their polymer conjugates or by release of the stereoisomer peptide or their polymer conjugates beyond the stomach environment, such as in the intestine. Common inert ingredients used in enteric coatings include colorants and flavoring agents, and inert materials such as mannitol, sucrose, lactose, and inorganic salts as fillers. Disintegrants and binders may be included in the formulation of the drug into a solid dosage form and may include materials from natural products such as starch and gelatin. Alcohol solutions, lubricants, surfactants, cationic, and non-ionic detergents, can also be included during formulation. Controlled release oral formulations may be desirable. The formulated drug could be incorporated into an inert matrix which permits release by either diffusion or enteric coatings with delayed release effect, many of which are commercially available.

Another aspect of the present invention is that the stereoisomer peptide compounds and peptide-polymer compounds resist degradation by enzymes found in human blood, serum, or body secretions, compared to the natural unmodified peptides in L-form which are unstable and easily degraded by human fluids. Resistant to degradation is an important property that allows flexibility to determine an appropriate formulation and the potential for oral bioavailability.

Mucosal Delivery: Nasal, Sublingual, Vaginal, and Rectal Administration

Mucosal transmission of HIV-1 infection, mediated by exposure to infectious virus and/or cells within mucosal secretions, can occur within minutes, established within hours, and can be disseminated to draining lymph nodes within days. Therefore, a therapeutic drug must be produced and formulated to effectively penetrate the mucosa and target the earliest events in the establishment of HIV infection. Compositions for nasal, sublingual, rectal, and vaginal delivery of formulated stereoisomer peptide compounds in free form and multi stereoisomer peptide-polymer conjugate compounds are also contemplated in this invention. Epithelial cells in the mucosa take up molecules via endocytosis. Since the polymer-conjugates will enter epithelial cells via the endocytic pathway or passive delivery, there is potential to deliver the drugs carried by the polymer via the mucosa Nasal and sublingual delivery allows the passage of the formulated compounds to the blood stream directly after administering the therapeutic product to the nose or under the tongue, without the necessity for deposition of the product in the lung.

Formulations for nasal delivery include those with dextran or cyclodextran. Penetration-enhancers are also used to facilitate delivery. Standard excipients well known in the art can also be included in the formulation. Compositions for rectal or vaginal administration are preferably suppositories which may contain, in addition to the active substance, excipients such as cocoa butter or a suppository wax, and may include lubricants made of wax or oil. Since the compositions of this invention resist degradation by enzymes found in human blood, serum and body secretions, this property allows flexibility in the mode of administration as a topical HIV prophylactic for harsh mucosal environments. Natural peptides in L-form do not allow such routes of administration given their fast degradation by the enzymes present in human fluids.

Parenteral Delivery

This mode of administration is also considered here. Preparations for parenteral delivery are well known in the art and include standard sterile aqueous or non-aqueous solutions, suspensions, or emulsions. Non-aqueous solvents or vehicles may contain polyethylene glycol, propylene glycol, vegetable oils, gelatin, and injectable organic esters. Such dosage forms may also contain preserving, wetting, emulsifying, and dispersing agents. These formulations are sterilized by filtration by incorporating sterilizing agents into the compositions, by irradiating the compositions, or by heating the compositions. They can also be manufactured using injectable sterile water, or sterile medium, immediately before use.

The foregoing formulations and administration methods are intended to be illustrative and not limiting. It will be appreciated that other suitable formulations and modes of administration can be readily prepared and applied to the compounds described in this invention.

Dosages

The selected dosage depends on the desired therapeutic effect, on the route of administration, and on the duration of the treatment desired. An ordinary skilled worker, considering the therapeutic context, age, and general health of the recipient, will be able to ascertain proper dosing. Proper doses can also be determined from further studies conducted with the compounds of this invention. Physicians may initially use escalating dosages starting at a concentration that meet the requirements for each individual being treated in a clinical trial. Dosage may be administered to naïve HIV infected individuals i.e., untreated, or to HIV-1 infected patients that have been treated with antiretroviral therapy (e.g., HAART), or can be co-administered with the antiretroviral therapy to prevent increase of viral load in HIV-1 infected patients. As described above, many routes of administration may be used, and for this purpose, the administration of compounds via oral and mucosa routes is contemplated.

The stereoisomer peptide compounds and stereoisomer peptide-polymer conjugate compounds carrying the same or different D-peptides of this invention are designed and aimed to block entry and virus replication, and induce an immunogenic response. This is theoretically supported by the strong T cell epitopes predicted for the majority of the peptides, by their lack of homology to human proteins by sequence comparison, and by their unique physicochemical properties that are enhanced during the synthesis of the stereoisomer peptides. Experimental validation of these theoretically supported compounds can be carried out using in vitro assays with cultured human cells, and in vivo assays in mice or non-human primates to evaluate the effectiveness of the compounds in treating and preventing HIV-1 infection and potentially AIDS. The identification of peptides will now be described, as well as the synthesis of compositions with particular reference to examples in which D-peptides are coupled each to separate HPMA copolymers carrying a biodegradable linker and activated groups to create multi-targeted peptide polymer conjugate compounds comprising a subject matter of this invention.

EXAMPLES

Although the present invention has been described in terms of specific exemplary aspects and examples, it will be appreciated that the aspects disclosed herein are for illustrative purposes only and various modifications and alterations might be made by those skilled in the art without departing from the spirit and scope of the invention as set forth in the following claims.

Example 1

This example illustrates the identification of peptide labeled SEQ ID NO: 296, as an epitope with immunogenic potential. The sequence of HIV-1 gp160 protein from B strain HXB2 isolate was retrieved from ViralZone-UniProtKB/Swiss-Prot entries, and was analyzed using the NCBI BLAST algorithm, against the entire database of human protein sequences to determine potential regions in the HIV proteins with homologous regions that overlap with human protein sequences. The comparison analysis revealed a short sequence of about 20 amino acids in HIV gp120 protein that has no sequence homology with any human protein. This short sequence was then analyzed using epitope prediction algorithms (NetMHC and SYFPEITHI) resulting in the identification of three peptides (one 8 mer and two 9 mers) that strongly bind to a particular MHC allele.

Peptide SEQ ID NO: 296 is an example of one of the two nine-mers. This predicted strong T-cell epitope can be used as 'antigen' to create, together with other peptides, a multi-targeted therapeutic using the methods known in the art. This peptide is part of the group of 218 predicted T-cell epitopes constituting compounds of this invention.

Example 2

Synthesis of a Stereoisomer Peptide-Polymer Conjugate Compound

Figure 2:
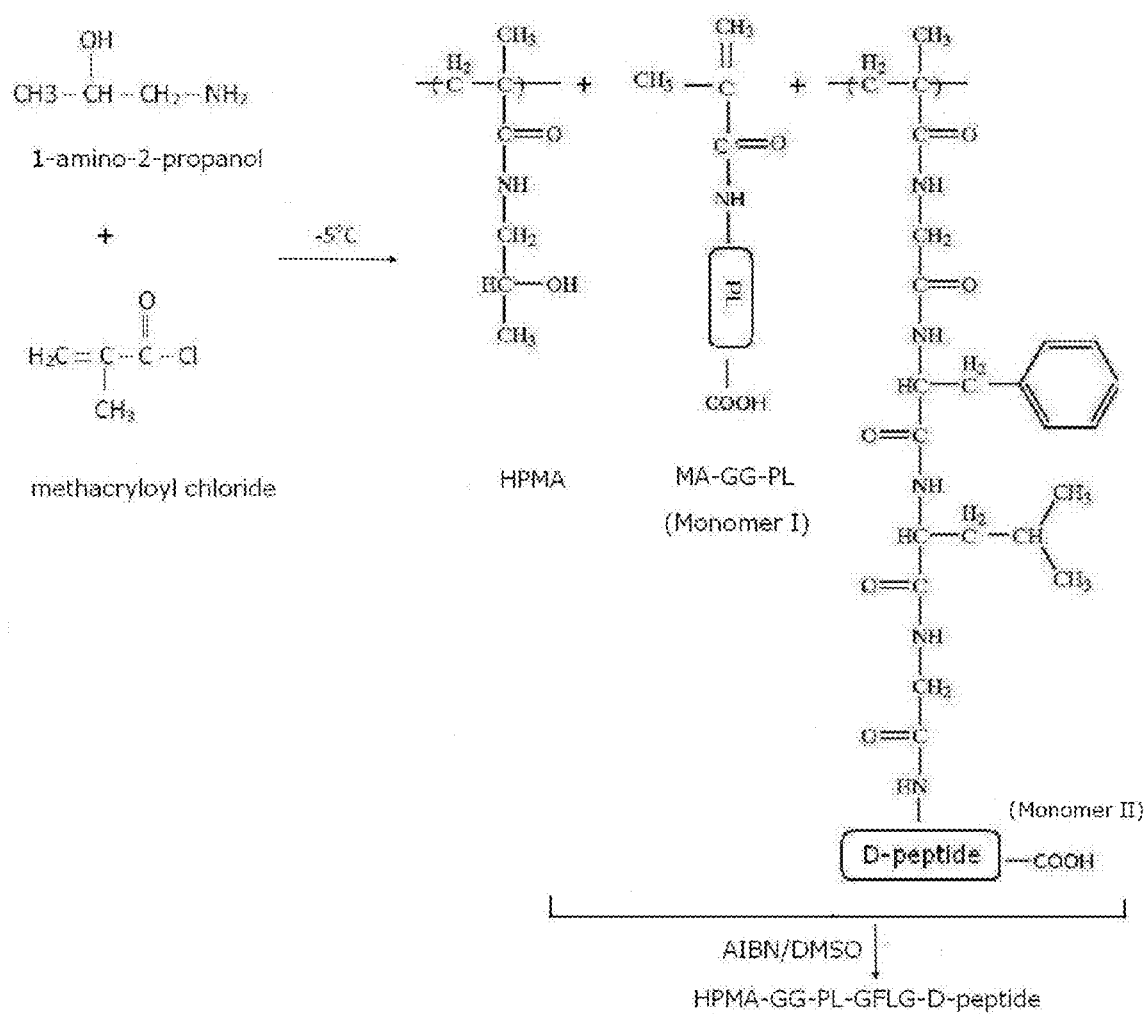
FIG. 2 shows synthesis of ligand-targeted i. This polymer conjugate is synthesized from polymerization of HPMA, Monomer I (MA-GG-PL) and Monomer II (MA-GFLG-D-peptide) in the presence of initiator AIBN and DMSO. This product is referred as stereoisomer peptide-polymer conjugate compound.

The synthesis of this ligand-targeted HPMA polymer-conjugate compound is carried out by copolymerization of MA-GFLG-D-peptide monomer and MA-GG-PL monomer to create a ligand-targeted HPMA-GFLG-D-peptide-GG-PL referred here as stereoisomer peptide-polymer conjugate compound (FIG. 2).

The monomers MA-GG-PL and MA-GFLG-D-peptide are first synthesized in separate reactions from the monomer precursors MA-GG-ONp to which PL is coupled, and MA-GFLG-ONp, to which a D-peptide is coupled by reaction with their activated ONp groups by nucleophilic attack. The monomers (20 mmol ONp) and peptides (PL or D-peptide) (26 mmol) are dissolved (separately) in 400 µl DMF is separate reactions; 30 ml of N,N-diisopropylethylamine (DIPEA) (177 mmol) diluted in DMF (1:1, v:v) is added to each mixture slowly dropwise with a Hamilton micro-syringe while stiffing the mixture at room temperature in the dark overnight. Unreacted ONp groups are deactivated (hydrolyzed) with 1-amino-2-propanol (2 ml), the mixture containing MA-GG-PL or MA-GFLG-D-peptide is diluted with deionized water. The solution is dialyzed and then lyophilized The exact PL or D-peptide content of each separate monomer is determined by amino acid analysis.

These monomers (MA-GG-PL and MA-GFLG-D-peptide) are then polymerized with HPMA via radical polymerization of the monomers using AIBN (2,2'-azobisisobutyronitrile) as the initiator in the presence of DMSO and the inert gas argon to obtain the ligand-targeted polymer conjugate HPMA-GG-LP-GFLG-D-peptide which contains one D-peptide and a peptide-ligand (see FIG. 2) The peptide-ligand (PL) can be an epitope, or a transduction peptide, or a receptor binding peptide, or a cell penetrating peptide guiding the polymer and its cargo to tissue, cells, or sub-cellular locations and deliver the D-peptide to the target site to compete with other molecules that interact with the target protein by binding, antagonizing or blocking a functional site.

In a particular embodiment of this invention, the polymer-conjugate compound can be prepared, for example, with the peptide labeled SEQ ID NO: 221 which is a cyclic peptide targeting HIV gp120, and SEQ ID NO: 298, which is a cell penetrating peptide (CPP) with alpha-helix structure, which mimics a domain of human lens ephithelium derived growth factor (LEDGF) and therefore is a competitive ligand. In another particular embodiment of this invention any of the peptides disclosed in this invention can be selected and combined to create the therapeutic compound targeting a single HIV protein.

These targeted conjugate compounds can be evaluated using in vitro and in vivo tests to determine their inhibitory potency and ability to inhibit, kill, or neutralize HIV depending on the assay. The polymer compounds synthesized by the methods described here are referred as novel stereoisomer peptide-polymer conjugate compounds, the subject matter of this invention.

Example 3

Synthesis of a Multi-Stereoisomer Peptide-Polymer Conjugates Compound

Figure 3:
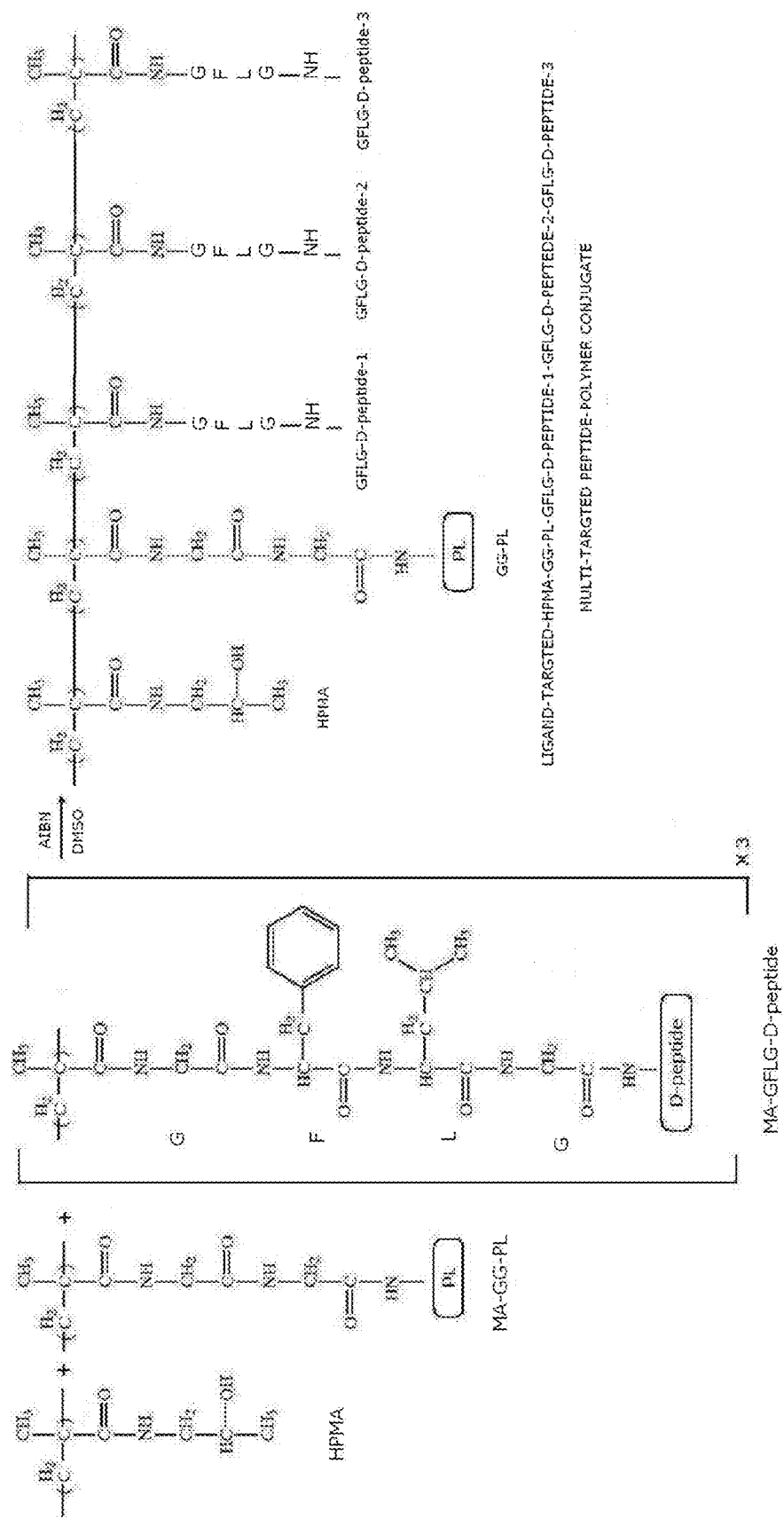
FIG. 3 shows synthesis of ligand-targeted HPMA-GG-PL-GFLG-D-peptide-1-GFLG-D-peptide-2-GFLG-peptide-3 polymer conjugate. This polymer conjugate compound is synthesized via radical copolymerization of HPMA in excess and the monomers MA-GG-PL, MA-GFLG-peptide-1, MA-GFLG-peptide-2, MA-GFLG-peptide-3 in the presence of the initiator 2,2'-azobisisobutironitrile (AIBN) and DMSO. This product is referred as multi stereoisomer peptide-polymer conjugate compound.

The synthesis of ligand-targeted HPMA containing three MA-GFLG-D-peptide monomers each with a different D-peptide and MA-GG-PL monomer with a peptide-ligand (PL) are copolymerized to create a multi-stereoisomer peptide-polymer conjugate compound of the form HPMA-GFLG-D-peptide-1-GFLG-D-peptide-2-GFLG-D-peptide-3-GG-PL (FIG. 3).

The pre-activated monomer precursors MA-GFLG-ONp and MA-GG-ONp containing ONp groups are prepared by adding to a solution of MA-GFLG-OH (10 mmol) or Ma-GG-OH (10 mmol) in 80 ml of DMF, a solution of 1.67 g of p-nitrophenol (12 mmol) in 20 ml of DMF under stirring and cooling to −10° C., followed by a solution of 2.5 g of DCC (12 mmol) in 8 ml of DMF. The two separate reaction mixtures are stirred for six hours at −10° C., and then overnight at 4° C. The precipitated by product is filtered off and the DMF removed by rotary evaporation. The residue is dissolved in EtOAc and the remaining byproduct is filtered off. EtOAc is evaporated to dryness. The final product is soaked in ether to remove excess p-nitrophenol. This procedure is repeated several times and the purity of MA-GFLG-ONp or MA-GG-ONp is checked by calculating the extinction coefficient in DMSO. MA-GFLG-ONp or MA-GG-ONp content is assessed by release of p-nitrophenol (ONp) from the polymer in 1.0 N NaOH by UV spectrophotometry (400 nm).

Coupling of D-peptides or the peptide-ligand (PL) to the activated para-nitrophenyl ester group in the linker (created by reaction of the carboxyl groups of a Gly residue, and conversion to p-nitrophenyl esters), is carried out via D-peptide amino groups by nucleophilic attack at the reactive ester groups forming amide linkages (covalent bonds) between the reactive p-nitrophenyl ester groups of the linker and the α-amino group of amino acids or the ε-amino group of Lys in the D-peptide. Alternatively, for cyclic peptides, coupling to the linker is carried out via the ε-amino group of a terminal Lys residue in the D-peptide. The ε-amino group of Lys is protected during peptide synthesis and then is de-protected to allow coupling to the activated linker. L-Lys residue may be incorporated during synthesis to peptides lacking this residue, or that require protected amino-terminal groups.

Coupling peptides to the monomer precursors MA-GFLG-ONp or MA-GG-ONp is carried out in separate reactions for each different D-peptide and PL. The copolymer precursor (20 mmol ONp) and D-peptide (26 mmol) or PL (26 mmol) are dissolved in 400 μl DMF. 30 ml of N,N-diisopropylethylamine (DIPEA) (177 mmol) diluted in DMF (1:1, v:v) is added slowly dropwise with a Hamilton micro-syringe while stirring the mixture at room temperature in the dark overnight. The reactive ester groups (i.e., carboxyl groups of residues converted to p-nitrophenyl ester) of the pre-activated monomer MA-GFLG-ONp or MA-GG-ONp are reacted with the D-peptide or the PL respectively, via nucleophilic attack of the amino groups (alpha-amino) forming amide linkages with the linker. D-peptides or PL can also be bound to the linker by the ε-amino group of L-Lys residue attached to the linker or to the ε-amino group of a D-Lys residue in the D-peptide. Unreacted ONp groups are deactivated (hydrolyzed) with 1-amino-2-propanol (2 ml), the mixture containing the final product MA-GFLG-D-peptide or MA-GG-PL is diluted in deionized water. Each separate monomer solution is dialyzed intensively and then lyophilized. For a polymer compound with three different D-peptides and one PL, four separate reactions are prepared. The exact content of PL or D-peptide in a particular monomer is determined by amino acid analysis.

Polymerization of the three monomers, with different D-peptides and one peptide-ligand (PL) is carried out by copolymerization of HPMA with the monomers MA-GFLG-D-peptide-1, MA-GFLG-D-peptide-2, MA-GFLG-D-peptide-3, and MA-GG-PL in acetone in the presence of AIBN as initiator; HPMA and monomers are reacted at a ratio 10:1 respectively. Briefly, radical precipitation copolymerization is carried out using a mixture of the above monomers at various molar ratios using the initiator 2,2'-azobisisobutironitrile (AIBN) and DMSO. The solution containing HPMA and monomers in acetone is mixed with the initiator, transferred to an ampoule, bubbled with nitrogen for 5 min, and sealed and placed in an oil bath at 50° C. for 24 hours under stirring. After 24 hours the copolymers would precipitate out of solution and the ampoules are cooled to room temperature and placed in the freezer for 20 minutes to increase the yield of the precipitated polymer further. The copolymers are filtered off, dissolved in methanol, and precipitated in ether. After filtration and washing with ether the polymer is dried under vacuum. The ligand-targeted HPMA-GFLG-D-peptide-1-GFLG-D-peptide-2-GFLG-D-peptide-3-GG-PL polymer conjugate in purified form is analyzed by size exclusion chromatography.

In a particular embodiment, the multi-targeted polymer-conjugate compound can be prepared, for example, with the peptides labeled SEQ ID NO: 297, which is a cyclic peptide targeting gp41; SEQ ID NO: 288, which is a cyclic peptide targeting HIV integrase; SEQ ID NO: 221 which is a cyclic peptide targeting HIV gp120, and SEQ ID NO: 265 (the peptide-ligand), which is a modified HIV Tat transduction domain or cell penetrating peptide with alpha-helix structure. Any of the peptides disclosed in this invention, however, can be selected and combined to create multi-targeted therapeutic compounds to target multiple HIV proteins. These multi-targeted polymer-conjugate compounds can be evaluated using in vitro and in vivo tests to determine their inhibitory potency and ability to neutralize, inhibit, or kill HIV.

Example 4

Figure 4:
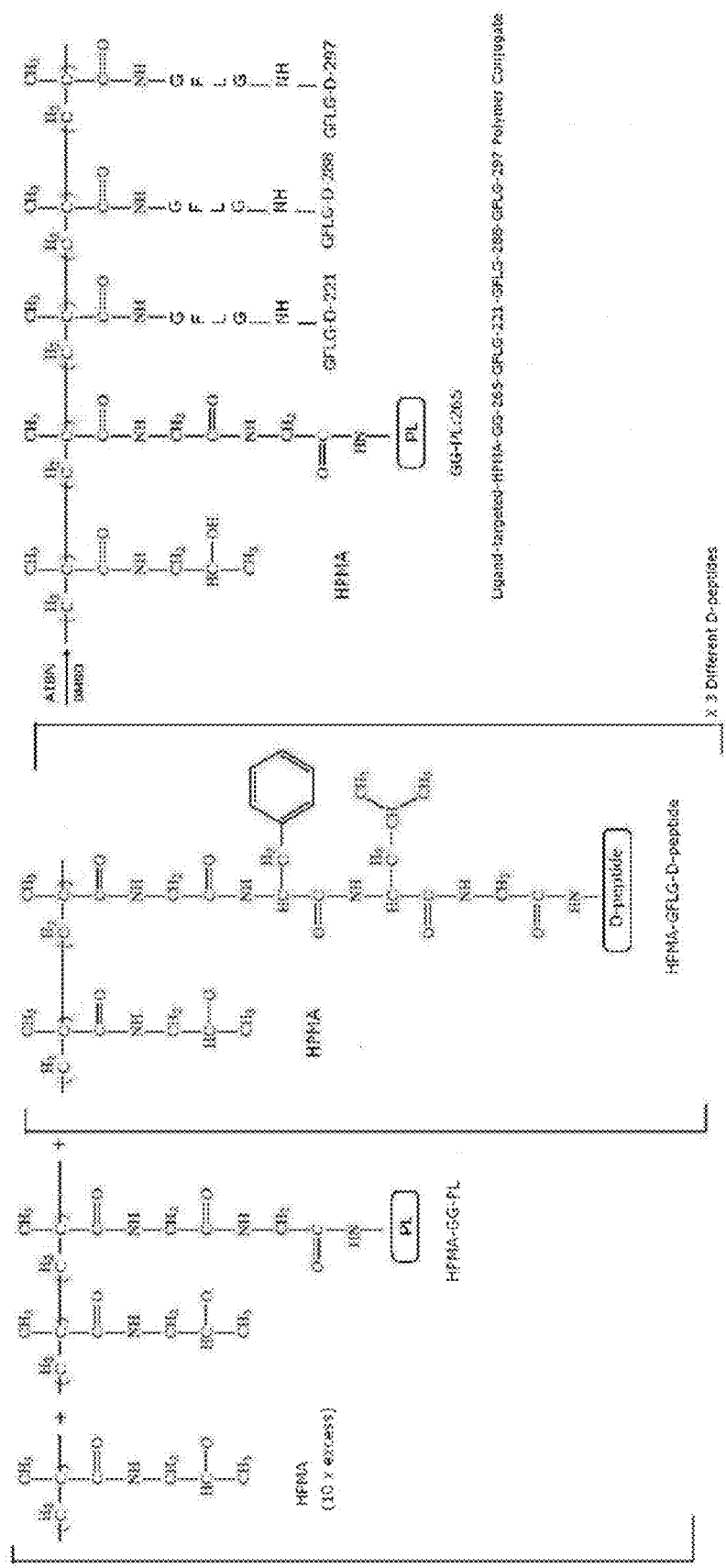
FIG. 4 shows synthesis of ligand-targeted HPMA-GG-PL-GFLG-D-peptide-1-GFLG-D-peptide-2-GFLG-peptide-3 polymer conjugate starting from HPMA polymers. This polymer conjugate is synthesized by copolymeization of polymers HPMA-GG-PL, HPMA-GFLG-peptide-1, HPMA-GFLG-peptide-2, HPMA-GFLG-peptide-3 in the presence of excess HPMA and the initiator AIBN and DMSO. This product is also referred as multi stereoisomer peptide-polymer conjugate compound.

Synthesis of polymer conjugates can also be carried out using preactivated monomer HPMA-GFLG-ONp which can be obtained directly from the supplier reducing the number of synthesis steps. Each different D-peptide is coupled by its terminal amino group to the active ONp group via nucleophilic attack in separate reactions to synthesize polymers carrying each a different D-peptide attached to a linker. Then all the separate polymers, including HPMA-GG-PL can be copolymerized in excess of HPMA (10×) by radical copolymerization in the presence of the initiator AIBN, DMSO and $N_2$ gas to obtain the ligand-targeted HPMA-GG-LP:265-GFLG-D-peptide: 297-GFLG-D-peptide:288-GFLG-D-peptide:221-polymer conjugate (FIG. 4).

The foregoing invention has been described in detail by way of description, illustration, and example, for the purpose of clarity of understanding. One skilled in the art will easily ascertain that certain modifications and variations of the compositions of the present invention, maybe practiced without departing from the spirit and scope of the appended claims.

References

Henikoff S, Henikoff J G (1989) Proc. Natl. Acad. Sci. USA 89:10915-9
Karlin S, Altschul S F (1993) Proc. Natl. Acad. Sci. USA, 90 (12): 5873 5787
Peters B et al. (2005) Vaccine 23: 5212-5224
Rammensee H et al. (1999) Immunogenetics, 50(3-4):213-219
Nielsen M et al. (2003) Protein Sci, 12, 1007-1017
Sylvester-Hvid C et al. (2004) Tissue Antigens. 63(5):395-400
Barany and Merrifield (1963) Solid-Phase Peptide Synthesis; pp. 3 284 in: The Peptides: Analysis, Synthesis, and Biology. Vol. 2: Special Methods in Peptide Synthesis, Part A
Stewart, J M, Young, J D (1984) Solid phase peptide synthesis (2nd Ed.) Rockford: Pierce Chemical Company. P. 91
Wuts P G M and Greene T W (2007) Greene's Protective Groups in Organic Synthesis, 4$^{th}$ ed., John Wiley & Sons, Inc.
Bulaj G, Olivera B M 2008. Antioxid Redox Signal. 10(1): 141-55
Kopeček J, BažilováH (1973) Europ. Polym. J. 9 (1973) 7-14
BohdaneckýM et al. (1974) Europ. Polym. J. 10 405-410

What is claimed is:

1. A multi-peptide-polymer conjugate, comprising stereoisomer and chemically modified forms of two or more peptides conjugated to a polymer via a linker, each peptide is selected from the group consisting of SEQ ID NO: 220-227, 229-231, 233 and 234, mimicking HIV-1 proteins selected from the group consisting of gag, p24, p2p7p1 p6, protease, integrase, Vif, Tat, glycoproteins gp120 and gp41, Nef, Vpu, and reverse transcriptase, wherein said polymer is an effective delivery system, and wherein said multi-peptide-polymer conjugate targets HIV-1.

2. The multi-peptide-polymer conjugate of claim 1, wherein said stereoisomer peptides comprise L- and D-amino acids.

3. The multi-peptide-polymer conjugate of claim 1, wherein said stereoisomer peptides comprise D-amino acids.

4. The multi-peptide-polymer conjugate of claim 1, wherein said peptides in their stereoisomer and chemically modified forms have acetylated and amidated ends.

5. The multi-peptide-polymer conjugate of claim 1, wherein said two or more stereoisomer peptides comprise 1-3 intramolecular bonds.

6. The multi-peptide-polymer conjugate of claim 5, wherein said intramolecular bonds are disulfide bonds, amide bonds, or thio-ether bonds forming a cyclic structure.

7. The multi-peptide-polymer conjugate of claim 1, wherein said polymer is N-(2-Hydroxypropyl) methacrylamide.

8. The multi-peptide-polymer conjugate of claim 1, wherein said peptide linker is selected from the group consisting of Phe-Lys; Gly-Gly-Phe-Lys; and Gly-Phe-Leu-Gly.

9. The multi-peptide-polymer conjugate of claim 8, wherein Gly-Phe-Leu-Gly is a protease-susceptible and cleavable linker.

10. The multi-peptide-polymer conjugate of claim 1, wherein at least one stereoisomer peptide is a peptide-ligand.

11. The conjugate of claim 1, wherein said two or more peptides target different HIV-1 proteins.

12. The conjugate of claim 11, wherein said different HIV-1 proteins are the glycoproteins gp120 and gp41.

13. The conjugate of claim 1, further comprising a peptide selected from the group consisting of SEQ ID NO: 219, 228 and 232.

14. A composition comprising the conjugate of claim 1 and a diluent, solubilizer, emulsifier, preservative, adjuvant and/or carrier, wherein said composition can be administered by the oral, parenteral, topical, transdermal, mucosal or pulmonary route.

* * * * *